(12) United States Patent
Woudenberg et al.

(10) Patent No.: US 9,182,322 B2
(45) Date of Patent: Nov. 10, 2015

(54) MICROFLUIDIC MIXING AND REACTION SYSTEMS FOR HIGH EFFICIENCY SCREENING

(71) Applicant: Fluidigm Corporation, South San Francisco, CA (US)

(72) Inventors: Tim Woudenberg, Moss Beach, CA (US); Jing Wang, South San Francisco, CA (US); Hou-Pu Chou, Sunnyvale, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 14/091,344

(22) Filed: Nov. 27, 2013

(65) Prior Publication Data
US 2014/0308178 A1    Oct. 16, 2014

Related U.S. Application Data

(63) Continuation of application No. 13/057,958, filed as application No. PCT/US2009/052726 on May 9, 2011, now Pat. No. 8,617,488.

(60) Provisional application No. 61/087,075, filed on Aug. 7, 2008.

(51) Int. Cl.
| | |
|---|---|
| *G01N 15/06* | (2006.01) |
| *G01N 33/00* | (2006.01) |
| *G01N 33/48* | (2006.01) |
| *G01N 1/28* | (2006.01) |

(Continued)

(52) U.S. Cl.
CPC ............... *G01N 1/28* (2013.01); *H04W 76/06* (2013.01); *H04W 4/005* (2013.01)

(58) Field of Classification Search
USPC .............................. 422/502, 503, 504; 436/43
See application file for complete search history.

(56) References Cited

U.S. PATENT DOCUMENTS

| | | | |
|---|---|---|---|
| 6,540,895 | B1 | 4/2003 | Spence et al. |
| 6,706,519 | B1 | 3/2004 | Kellogg et al. |

(Continued)

FOREIGN PATENT DOCUMENTS

| | | |
|---|---|---|
| WO | 2007/033385 A2 | 3/2007 |
| WO | 2007/044091 A2 | 4/2007 |

(Continued)

OTHER PUBLICATIONS

International Search Report mailed on Oct. 5, 2009 for International Patent Application No. PCT/US2009/052726, 1 page.

*Primary Examiner* — Brian J Sines
(74) *Attorney, Agent, or Firm* — Kilpatrick Townsend & Stockton LLP

(57) ABSTRACT

Microfluidic devices are described that include a rigid base layer, and an elastomeric layer on the base layer. The elastomeric layer may include at least part of a fluid channel for transporting a liquid reagent, and a vent channel that accepts gas diffusing through the elastomeric layer from the flow channel and vents it out of the elastomeric layer. The devices may also include a mixing chamber fluidly connected to the fluid channel, and a control channel overlapping with a deflectable membrane that defines a portion of the flow channel, where the control channel may be operable to change a rate at which the liquid reagent flows through the fluid channel. The devices may further include a rigid plastic layer on the elastomeric layer.

4 Claims, 21 Drawing Sheets

(51) Int. Cl.
*H04W 76/06* (2009.01)
*H04W 4/00* (2009.01)

(56) References Cited

U.S. PATENT DOCUMENTS

| | | | |
|---|---|---|---|
| 6,729,352 B2 | 5/2004 | O'Connor et al. |
| 6,885,982 B2 | 4/2005 | Harris et al. |
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Van Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,307,802 B2 | 12/2007 | Unger |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 2002/0028480 A1 | 3/2002 | Maher et al. |
| 2003/0064507 A1 | 4/2003 | Gallagher et al. |
| 2004/0180377 A1 | 9/2004 | Manger et al. |
| 2005/0053952 A1 | 3/2005 | Hong et al. |
| 2005/0145496 A1 | 7/2005 | Goodsald et al. |
| 2006/0172408 A1 | 8/2006 | Quake et al. |
| 2006/0233674 A1 | 10/2006 | Nelson |
| 2006/0281183 A1 | 12/2006 | Sun et al. |
| 2007/0041878 A1 | 2/2007 | Bryning et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0168066 A1 | 7/2009 | Hansen et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |

FOREIGN PATENT DOCUMENTS

| | | |
|---|---|---|
| WO | 2008/043046 A2 | 4/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |

PDMS   FLOW

MICROFLUIDIC MIXING AND REACTION SYSTEMS FOR HIGH EFFICIENCY SCREENING

CROSS-REFERENCES TO RELATED APPLICATIONS

This application is a continuation of U.S. application Ser. No. 13/057,958, filed May 9, 2011, which is a national phase of International Patent Application No. PCT/US2009/052726, filed Aug. 4, 2009, which claims the benefit of U.S. Provisional Application No. 61/087,075, filed on Aug. 7, 2008. The entire disclosures of which are incorporated herein by reference.

BACKGROUND

High density microfluidic devices are useful in a wide range of research, diagnostic and synthetic applications, including immunoassays, nucleic acid amplification and genomic analysis, cell separation and manipulation, and synthesis of radionuclides, organic molecules, and biomolecules. The advantages of microfluidic devices include conservation of reagents and samples, high density and throughput of sample analysis or synthesis, fluidic precision and accuracy, and a space reduction accompanying the replacement of counterpart equipment operating at the macrofluidic scale.

Efforts are being made to integrate microfluidic devices with existing high density and throughput testing equipment. Much of this conventional equipment relies on microtiter plates for holding, mixing, forming and reacting samples. The plates are typically flat glass or plastic trays in which an array of circular reagent wells are formed. Each well can typically hold between from a few microliters to hundreds of microliters of fluid reagents and samples, which may be loaded into the wells with automated delivery equipment. Plate readers are used to detect biological, chemical and/or physical events in the fluids placed in each well.

As the fields of combinatorial chemistry and high throughput screening have grown, so has equipment and laboratory instrumentation that has been designed to fill, manipulate and read microtiter plates. Unfortunately, independent equipment makers made little effort develop systems that were cross-compatible with the systems of other manufacturers. By the mid-1990s, the Society for Biomolecular Screening (SBS) formed a standards group to address these cross-compatibility problems. A final set of standards was published by SBS and the American National Standards Institute 2003.

These standards define the overall dimensions of a compliant microtiter plate, as well as the diameter, depth and spacing of the reagent wells in the plate. The plates may include 96, 384, 1536, etc., wells arranged in a 2:3 rectangular matrix. While some manufacturers have made plates packing even larger numbers of reagent wells into the dimensions of an SBS-formatted plate, the small-sizes of the wells can make filling and reading the plates more difficult.

The manipulation of fluid volumes on the order of nanoliters and picoliters has required many new discoveries and design innovations. There are fundamental differences between the physical properties of fluids moving in large channels and those traveling through micrometer-scale channels. See, e.g., Squires and Quake, 2005, *Rev. Mod. Phys.* 77, 977-1026; Stone et al., 2004, *Annu. Rev. Fluid Mech.* 36:381-411; and Beebe et al., 2002, *Ann. Rev. Biomed. Eng.* 4:261-86. For example, at a microfluidic scale the Reynolds number is extremely small, reflecting a difference in the ratio of inertial to viscous forces compared to fluids at macroscale. Fluids flowing in microfluidic systems exhibit reduced turbulence, electro-osmotic and laminar flow properties, and in other ways behave differently than observed at a macroscale.

Thus, there is a need for integrating microfluidic fluid delivery methods with conventional high efficiency and throughput testing equipment to effect efficient flow, containment and mixing of microfluids in this equipment. There is also a need to realize these microfluidic delivery methods in devices that can substitute for SBS formatted microtiter plates, so they can take advantage of the large amount of SBS-formatted equipment and instrumentation that is currently in use. These and other needs are addressed by the present invention.

BRIEF SUMMARY

Embodiments of the invention include microfluidic devices having a rigid base layer, and an elastomeric layer on the base layer. The elastomeric layer may include at least part of a fluid channel for transporting a liquid reagent, and a vent channel that accepts gas diffusing through the elastomeric layer from the flow channel and vents it out of the elastomeric layer. The devices may also include a mixing chamber fluidly connected to the fluid channel, and a control channel overlapping with a deflectable membrane that defines a portion of the flow channel, where the control channel may be operable to change a rate at which the liquid reagent flows through the fluid channel. The devices may further include a rigid plastic layer on the elastomeric layer.

Embodiments of the invention also include microfluidic devices having a rigid base layer, an elastomeric layer on the base layer. The elastomeric layer may include a vent channel that accepts gas diffusing through the elastomeric layer and vents it out of the elastomeric layer. The devices may also have a rigid plastic layer on the elastomeric layer. A plurality of reaction chambers may be arranged in a array of rows and columns in the devices, where gases but not liquids may diffuse from the reaction chambers to the vent channel. The devices may have a first fluid bus coupled to a row of the reaction chambers, and having a first bus inlet to accept a first fluid from a first fluid source external to the microfluidic device. The devices may also have a second fluid bus coupled to a column of reaction chambers, and having a second bus inlet to accept a second fluid from a second fluid source external to the microfluidic device.

Embodiments of the invention still further include methods of filling a reaction chamber in a microfluidic device. The methods may include providing a microfluidic device comprising an elastomeric layer positioned between two gas impermeable layers. The device may include a slug channel formed in the elastomeric layer and fluidly coupled to the reaction chamber, and a vent channel also formed in the elastomeric layer. The methods may also include isolating a first portion of the slug channel from the second portion of the slug channel by closing a first valve partitioning the first and second portions of the slug channel. The first portion of the slug chamber may be filled with a first fluid, and the second portion of the slug chamber with a second fluid. A second valve between the slug channel and the reaction chamber may be opened to inject at least a portion of the first and second fluids into the reaction chamber. The injection of the first and second fluids displaces at least a portion of gases in the reaction chamber. At least a portion of the displaced gases that have diffused through the elastomeric layer from the reaction chamber may be transported in the vent channel.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION

I. Overview

Figure 1:
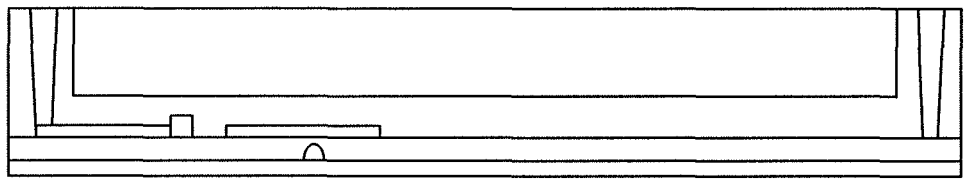
FIG. 1 shows a microfluidic device according to embodiments of the invention.

Microfluidic devices are described for high efficiency and throughput equipment having research, diagnostic and synthetic applications, among others. These devices may be used with real-time PCR equipment, fluorescent plate readers, robotic plate handlers, pipetting robots, and equipment designed to load, manipulate and read microfluidic devices, among other applications.

Embodiments of the microfluidic devices may include an elastomeric layer positioned between two rigid layers. One of the rigid layers may be a base layer that provides a thermal, electrical, physical, and/or optical interface between the device and surrounding equipment. For example, if the microfluidic device is used in a PCR application, the base layer may a thermally conductive IHS layer.

The rigid layer opposite the base layer may be a translucent plastic layer that includes openings (e.g., wells) to accept samples and reagents delivered to the device. This layer may be made out of relatively inexpensive injection molded or thermoset plastic. The mould for this layer may also include recesses, channels and other structures that form part of fluid flow and mixing infrastructure of the device. For example, a surface of this layer that comes in contact with the elastomeric layer may include recesses that form part of mixing/reaction chambers, flow channels, and/or control channels in the microfluidic device.

The elastomeric layer may be a single layer, or a plurality of layers bonded together. The elastomeric layer may include structure for all or part of the mixing/reaction chambers, flow channels, control channels, vent channels, deflectable membranes, check valves, and other components of the device.

The footprint of the device and the arrangement of the mixing/reaction chambers may be compatible with an established format for automated laboratory equipment, such as the SBS format. Integrating the microfluidic devices with preexisting sample delivery and high efficiency and throughput testing equipment combines advantages from both fields. Microfluidic systems have fewer moving parts and simpler operational logistics than robotic fluid delivery systems. In general, the microfluidic systems cost less to manufacture and require less maintenance and repair. In addition, microfluidic systems can be manufactured with smaller sized conduits and chambers, allowing them to deliver smaller volumes of samples, reagents, etc., than practicable with, for example, pipetting robots. This can reduce the costs and waste products generated for large screening studies involving thousands or more combinations of reagents and samples. The small volumes can also make screening and combinatorial studies practical when only a small amount of a sample is available.

Smaller component dimensions also permit more densely packed arrangements of the reaction sites. For example, two, four, eight, or more microfluidic reaction chambers (each defining a reaction site) may be packed into the interrogation area of a single site for a standardized high throughput screening device. This can allow the microfluidic device to achieve a twofold, fourfold, eightfold, or more, increase in the throughput rate using an existing screening device.

II. Definitions

The following definitions are provided to assist the reader. In some cases, terms with commonly understood meanings in the microfluidic arts are defined herein for clarity and/or for ready reference, and the inclusion of such definitions herein should not be construed to represent a substantial difference over the definition of the term as generally understood in the art.

As used herein, "mixing" has its usual meaning. Two (or more) different solutions (e.g., aqueous solutions) are completely mixed when they are combined to produce a single homogenous solution. Put differently, a first solution containing a first solute and a second solution containing a second solute produce, when completely mixed, a solution in which both solutes are homogenously distributed. On a microfluidic (low Reynolds number) scale, mixing is almost exclusively diffusional rather than turbulent. Without intending to be bound by a specific mechanism, the present invention provides superior mixing by increasing the contact area (interface) between the solutions relative to prior microfluidic methods of combining solutions. Using methods of the invention, a larger interface between solutions is achieved both in the slug channel and reaction chamber. By increasing the surface area, the rate of diffusional mixing is increased.

As used herein, "flow channel" means a microfluidic flow channel. A microfluidic flow channel is a tube through which a solution (e.g., an aqueous solution) can flow. The flow channel may have a circular, rectangular or other shape cross section(s), and may have differing cross-sections or dimensions along its length. A microfluidic flow channel is characterized by cross-sectional dimensions less than 1000 microns. Usually at least one, and preferably all, cross-sectional dimensions are less than 500 microns. Frequently at least one, and preferably all, cross-sectional dimensions are less than 250 microns.

As used herein, a "segment" of a flow channel refers to a section or a specified region of a flow channel. Usually the segment is bounded by specific structural elements of the flow channel, and thus can be defined by reference to the structural elements. Examples of structural elements include valves, changes in channel shape or dimensions (for example a change from a rectangular cross-section to a circular cross section, as when moving from a horizontal channel segment into a vertical fluid communication via), change in direction (for example a "L"-shaped flow channel can be described as having two orthogonally oriented flow channel segments), junctions with other channels, junctions with other elements (e.g., reaction chamber) and the like. Specified flow channel segments can overlap. For example, in a flow channel with four valves designated a, b, c and d, flow channel segments can include a-b, a-d, a-d, b-c, b-d, and c-d. It will be apparent that a flow channel can also be referred to as a channel segment, bounded by the termini of the channel.

As used herein, "linking segment" refers a channel segment that links channel segments in different layers of a device or links a channel segment in one layer to a reaction chamber in a different layer(s). A "fluid communication via" is an example of a linking segment and refers to flow channel segment in an multilayer device that connects fluidic elements in different layers of the device and which is fabricated by drilling, ablating (laser punching), molding or embossing a tunnel through the material from which the device is constructed. Another example of a linking segment is a connecting channel created using a replica molding process such as that described in Anderson et al., U.S. Pat. No. 6,645,432.

As used herein, a "flow path" describes a channel segment or series of channel segments through which a solution can flow and, more specifically, through which solution flows during the operation of a device.

As used herein, the terms "layer" and "level" have the standard meaning in the art. The terms are used interchangeably when referring to the position of flow channel segments, control channels, reaction chambers and other elements of a microfluidic device. In some microfluidic devices channels are located in different planes of the device. For example, an on/off elastomeric valve can be fabricated by locating a control channel in one plane so that it crosses the path of a flow channel in an adjacent different plane. The term "layer" also reflects the method of fabrication of such devices, in which layers of elastomeric structures may be bonded to each other.

The term "blind filling" refers to the process of instilling a solution into a channel or chamber that does not have a functional exit through which an aqueous solution can flow. A chamber or channel may have no functional exit because all potential exit flow channels are blocked by closed or impassable valves, or because there are no exit flow channels (e.g., no channels contiguous with the chamber other then the flow channel though which solution enters the chamber). In the latter situation, a reaction chamber into which the solution is instilled can be called a "dead-end" reaction chamber. A flow channel, or flow channel segment, into which solution is being instilled can be called a "dead-end" or "blind" channel. Blind filling takes advantage of the permeability of the material (e.g., elastomeric materials) defining at least a portion (e.g., at least a portion of one side) of the flow channel or at least a portion (e.g., at least a portion of one wall) of a chamber to gas and not to liquid.

As used herein, the term "check valve" refers to a one-way valve that resists or prevents reverse flow through a microfluidic channel.

As used herein, a "bus line" (e.g., reagent bus line or sample bus line) refers to a flow channel or flow path in fluid communication with a source reservoir (e.g., reagent source reservoir or sample source reservoir) and with slug channels or multiple unit cells. The sample bus line is arranged so that a sample solution can flow from a sample source reservoir to slug channels without flowing though reagent bus lines or reagent input lines. The reagent bus line is arranged, if present, so that a reagent solution can flow from a reagent source reservoir to slug channels without flowing though sample bus lines.

Several terms, examples of which follow, are used for convenience in the discussion and have meaning relative to each other.

The terms "vertical" and "horizontal" are used herein to describe the relationships of device elements, such as channels, and have meaning relative to each other. It is often convenient to fabricate a microfluidic device that is cuboid with one dimension being considerably shorter than the other two dimensions and operate the device so that the short dimension (height) is vertically oriented relative to the earth and the other two dimensions (length and width) are horizontally oriented. In such a design a channel segment in which solution flows in the height dimension may be termed "vertical" and a channel segment in which solution flows in the width and/or length dimension may be termed "horizontal." However the use of these terms does not require a cuboid-shaped device or operation in such an orientation.

The terms "sample solution" and "reagent solution" are used throughout the description to refer to solutions that are mixed using the methods and devices of the invention. Typically a sample solution contains biological material from a particular source (e.g., human, animal, lake, food, etc.) and a reagent solution contains compound used for analysis of a property of the sample. However, these terms are used for convenience and the invention is not limited to a narrow interpretation of a "sample" and a "reagent." The invention provides for methods and devices for the thorough mixing of two solutions. Thus, the term sample solution(s) could interchanged with "first solution(s)," "reagent solutions(s)," "analyte solutions," "second solution(s)," etc., and the term reagent solution(s) could interchanged with "first solution(s)," "sample solutions(s)," "analyte solutions," "second solution(s)," etc. For example, a first solution could contain one reactant and the second solution could contain a different reactant that when mixed chemically combine to produce a reaction product.

As used herein, the terms "column" and "row" have their usual meanings and are used in descriptions of unit cell arrays. However, no further function or structure is intended by such references. For example, reference to reagent bus lines that link columns of unit cells and sample bus lines that link rows of unit cells would be equivalent to a reference to reagent bus lines that link rows of unit cells and sample bus lines that link columns of unit cells. Moreover, unless otherwise specified, rows and columns do not require strict alignment. Unit cells in a row, for example, can be staggered or offset from a central line relative to each other. Further, the term "array" is not limited to arrangements of rows and column. For example, unit cells in a unit cell array could be arranged in concentric circles, along radii of the outermost circle.

III. Exemplary Microfluidic Devices

FIG. 1 shows a microfluidic device according to embodiments of the invention. The device shown shows an elastomeric layer positioned between a rigid base layer and a rigid plastic top layer. In the cross-sectional view show in FIG. 1, wells are formed in the peripheral sidewalls of the rigid plastic layer. One or more of these wells can provide an inlet to deliver a fluid sample or reagent to the microfluidic device. For example, the wells may be formed to accept the tip of a pipette that is coupled to a sample or reagent source (not shown). In addition, one or more of the wells may act as an outlet for a vent channel to allow displaced gases to exit the elastomeric layer.

In the embodiment shown, the rigid plastic layer also includes some additional structure on the surface of the layer that contacts the elastomeric layer. This structure includes recesses for a flow channel and mixing/reaction chamber that are fluidly coupled. It also includes a recess for another flow channel. In the embodiment shown, the top and sidewall surfaces of the channels and chamber are formed in the rigid plastic, while their bottom surfaces are formed by the adjacent elastomeric layer. Because the bottom surfaces are exposed to the elastomeric layer, gases displaced during a blind fill operation can pass through these surfaces into the elastomeric layer. A portion of these displaced gases that pass into a vent channel (not shown) will be transported out of the elastomeric layer.

The elastomeric layer shown includes a cross-section of a control channel having a deflectable membrane formed integral with a top surface. The deflectable membrane may be deflected into the second flow channel formed in the rigid plastic layer by pressurizing the control channel. In an alternate embodiment, the second channel formed in the rigid plastic layer may function as a control channel, which forces the deflectable membrane down into channel formed in the elastomeric layer.

The base layer may be made from a rigid material suited for a particular application of the microfluidic device. For example, if the microfluidic device will be thermocycled in a PCR application, the base layer may be made from a thin layer of rigid plastic or metal (e.g. silicon) with good heat transfer properties.

Figure 2:
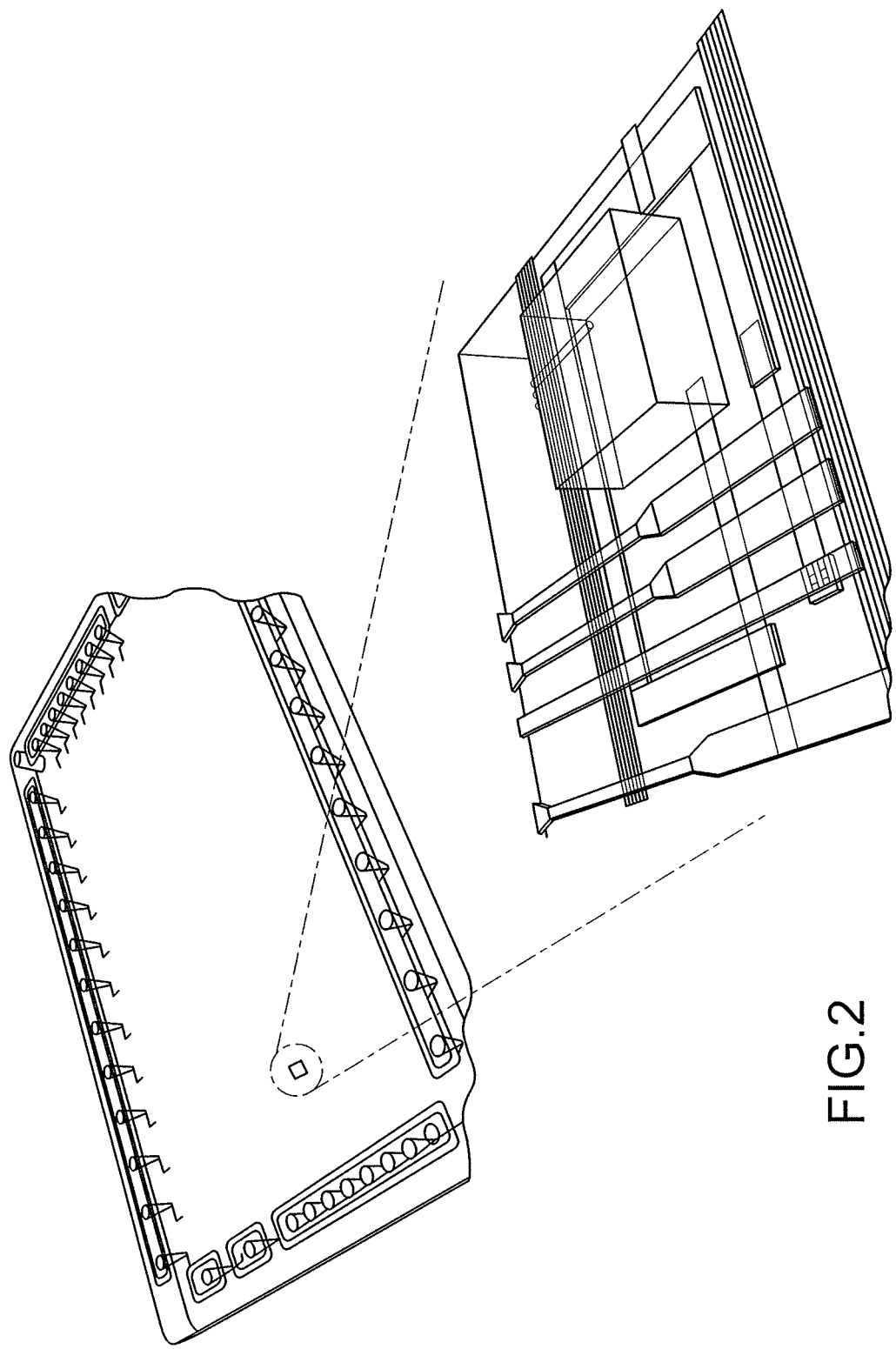
FIG. 2 shows a microfluidic device according to embodiments of the invention that includes an array of wells along the periphery and a magnified projection of a single mixing/reaction chamber unit.

FIG. 2 shows another embodiment of a microfluidic device having a rectangular shape and a plurality of wells peripherally distributed around the four sides of the rectangle. The bottom of each conically shaped well is coupled to a channel. For wells that supply samples and reagents to the mixing/reaction chambers, the channels are fluidly coupled to one or more of the mixing/reaction chambers. For wells that act as an outlet for displaced gases, the channels may be fluidly coupled to one or more vent channels. For wells that actuate deflectable membranes, the channels may be coupled to one or more control channels.

FIG. 2 also shows a magnified view of a mixing/reaction chamber unit near the middle of the microfluidic device. As can be inferred from the size of the area being magnified, there is space on the microfluidic device for several mixing/reaction chamber units. As discussed in more detail infra, these units may be arranged in an array in accordance with a formatting standard for high efficiency and throughput testing equipment, such as the SBS format.

Figure 3:
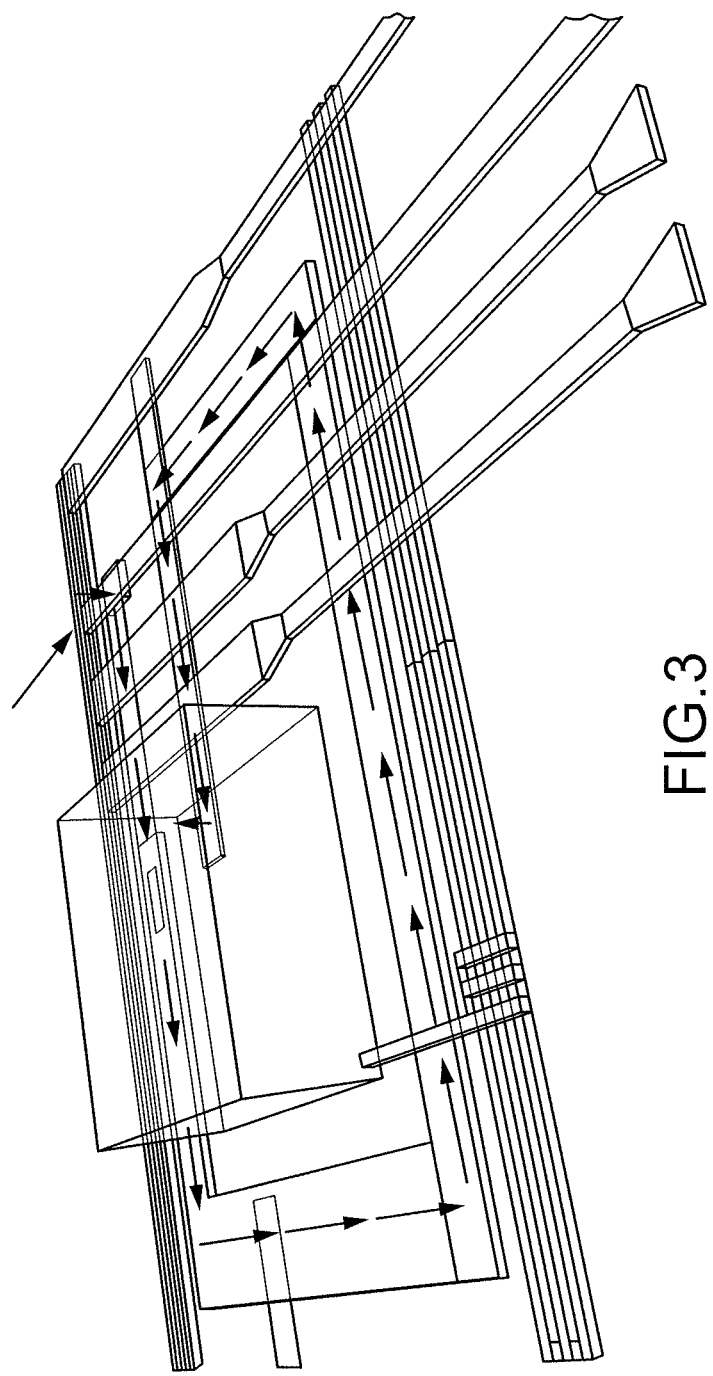
FIG. 3 shows a single mixing/reaction chamber unit according to embodiments of the invention with arrows indicating the direction of fluid flow into the unit.

FIG. 3 shows a mixing/reaction chamber unit similar to the one shown in the magnified section of FIG. 2. This unit includes the mixing/reaction chamber fluidly coupled to an underlying flow channel by a vertical via. Sample or reagent fluid from a reservoir source or fluid bus (not shown) flow through the flow channel in the direction of the arrows. In this embodiment, the fluid in the flow channel is first directed around the mixing/reaction chamber, and crosses a pair of parallel control channels. Then the fluid turns back around to travel underneath the middle of the mixing/reaction chamber before being directed up through the via into the chamber.

A vent line adjacent to the flow channel is used to capture displaced gases (e.g., air) from the flow line and the mixing/reaction chamber as they are filled with the sample or reagent fluid. In embodiments where the rigid base layer and rigid plastic top layer are made from gas-impermeable materials, the displaced gases are forced to diffuse through the gas permeable elastomeric layer. The vent channels are positioned to capture a fraction of these diffusing gases allowing them to be vented more easily out of the elastomeric layer (and usually out of the microfluidic device altogether).

In the embodiment shown in FIG. 3, the vent channel is crossed by a number of control channels. One or more control channel (not shown) may be used to close the vent channel from a well or other outlet that directs gases out of the elastomeric layer. In some applications, keeping the vent channel closed until a fluid loading even occurs may be advantageous to prevent excessive amounts of water vapor from escaping the elastomeric layer.

In embodiments of the mixing/reaction chamber unit shown in FIG. 3, an upper portion of the mixing reaction chamber and/or other structures may be formed in the rigid plastic top layer. For example, the top inside surface and sidewall surfaces of the chamber may be defined by the rigid plastic top layer, while the bottom inside surface may be defined by the top of the elastomeric layer. Similarly, the top and sidewall surfaces of the control channels may be defined by the rigid plastic top layer, and the bottom surface of the channels may be defined by the elastomeric layer. Embodiments may also include having a portion of the flow channel defined at least in part by the rigid plastic top layer while another portion is defined (partially or completely) by the elastomeric layer. For example, a portion of the flow channel in FIG. 3 may be defined by the rigid plastic top layer, and another portion of the flow channel underneath the mixing/reaction chamber may be partially or completely defined by the elastomeric layer. The two portions may be coupled by a via, or some other opening, in the top of the elastomeric layer.

Figure 4A:
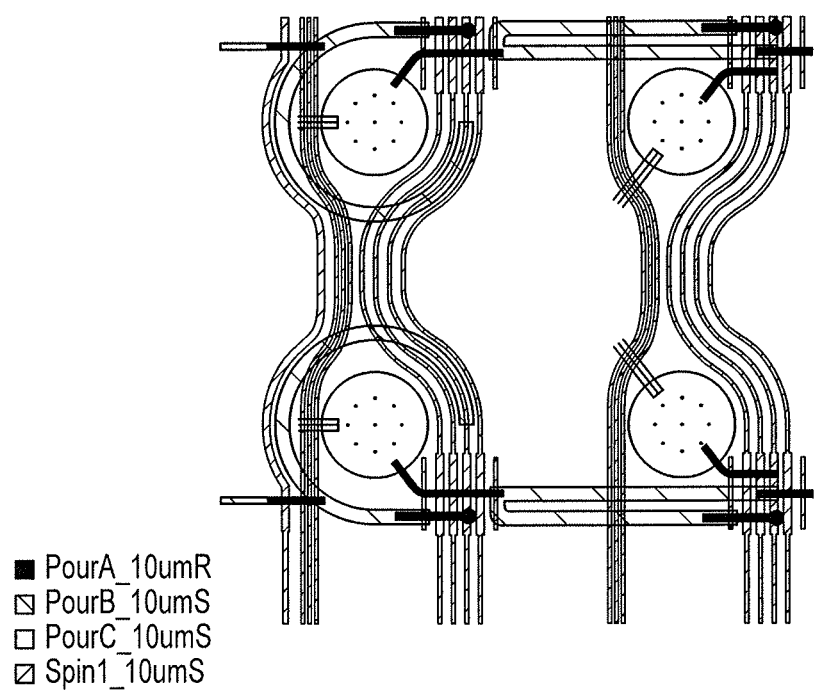
FIGS. 4A-B show a group of 4 mixing/reaction chamber units according to embodiments of the invention.
Figure 4B:
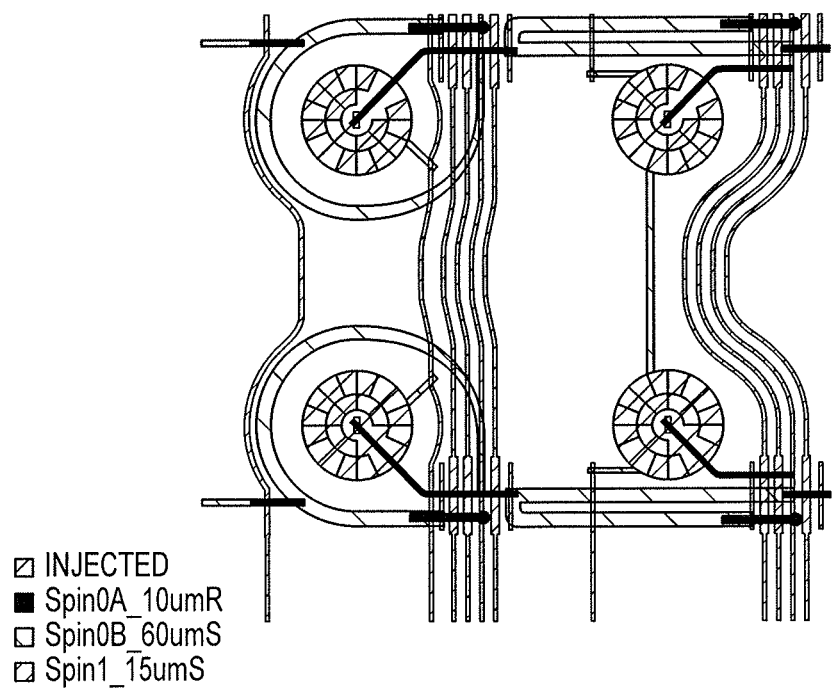

FIGS. 4A and B show a group of four mixing/reaction chambers arranged in a 2×2 array. In FIG. 4A the mixing/reaction chambers are completely defined in the elastomeric layer, while in FIG. 4B all but the bottom surface of the reaction chambers are defined by the rigid plastic top layer.

Exemplary Fluid Flow Regulation Structures

Embodiments include the regulation of fluid flow through the flow channels with the help of deflectable membranes that are actuated into and out of the flow channels by pressurizing and intersecting control channel. Details about regulating fluid flow by these structures and methods can be, among other places, in U.S. Pat. No. 6,408,878, filed Feb. 28, 2001, entitled "MICROFLUIDIC ELASTOMERIC VALVE AND PUMP SYSTEMS"; U.S. Pat. No. 6,899,137, filed Apr. 6, 2001, entitled "MICROFABRICATED ELASTOMERIC VALVE AND PUMP SYSTEMS"; U.S. patent application Ser. No. 09/724,784 filed Nov. 28, 2000, entitled "MICROFABRICATED ELASTOMERIC VALVE AND PUMP SYSTEMS"; and Ser. No. 09/605,520, filed Jun. 27, 2000, entitled "MICROFABRICATED ELASTOMERIC VALVE AND PUMP SYSTEMS."

Embodiments also include using microfluidic check valves as a supplemental or substitute method of regulating fluid flow the microfluidic devices. For example, FIGS. 5A and B show configurations of microfluidic check valves (VCK) positioned downstream and upstream of a valve (V1) that controls the fluid flow into a mixing/reaction chamber according to embodiments of the invention. Inclusion of the check valve proximal to the mixing/reaction chamber provides certain advantages. For example, in operation of an microfluidic device, after reagent and sample solutions are delivered to the reaction chamber, the chamber is often isolated, e.g., by closing valve V1, so that the reaction is contained in the reaction chamber. By using a microfluidic check valve the reaction chamber contents may be effectively contained in the chamber without the necessity of closing valve V1 and/or without the need to maintain valve V1 in the closed state for the duration of the reaction and/or duration of any analysis steps. This is especially useful when the microfluidic device is physically moved after the reaction chamber is filled (e.g., moved to a thermocycler or reader).

Figure 5A:
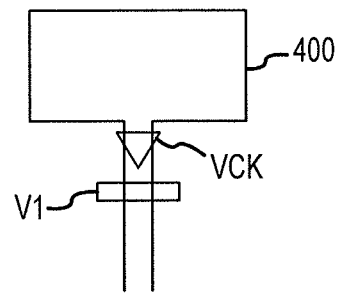
FIGS. 5A-C show alternative configurations of check valves in a mixing/reaction chamber unit according to embodiments of the invention.
Figure 5B:
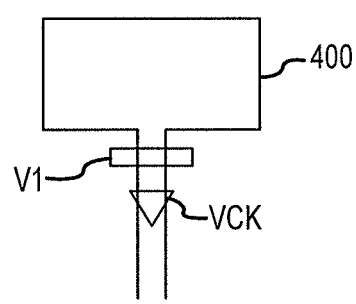

In FIG. 5A, the microfluidic check valve (VCK) is situated between a first valve (V1) and the mixing/reaction chamber to prevent reverse flow from the reaction chamber back into the flow channel, which is acting as a slug channel. In FIG. 5B, the check valve is positioned upstream from the first valve (V1) that opens and closes an inlet into the mixing/reaction chamber. The microfluidic check valve prevents the reverse flow from the chamber into back into the portion of the fluid channel upstream of the check valve. In this embodiment, the microfluidic check valve (VCK) may be placed as close a possible to the to valve (V1) to minimize the volume of sample and/or reagent solution in the slug path that is in fluid communication with the contents of the mixing/reaction chamber after the chamber is filled.

Figure 5C:
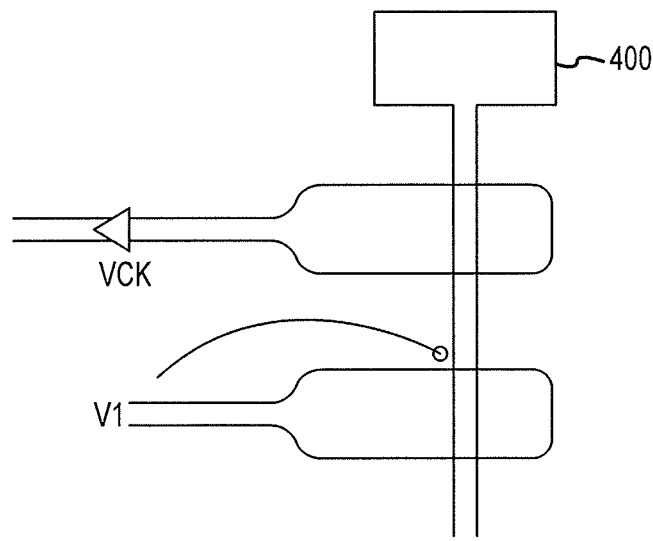

FIG. 5C shows an embodiment where the microfluidic check valve (VCK) is incorporated into a control channel instead of a flow channel. Check valves may be incorporated in a control channel so that pressure continues to be exerted in the control channel after it's disconnected from an initial pressurizing source. In FIG. 5C. the check valve (VCK) prevents a portion of the control channel overlapping the flow channel from depressurizing. Thus once pressurized, the control channel irreversibly closes the flow channel near the entrance to the reaction chamber (400).

Figure 6:
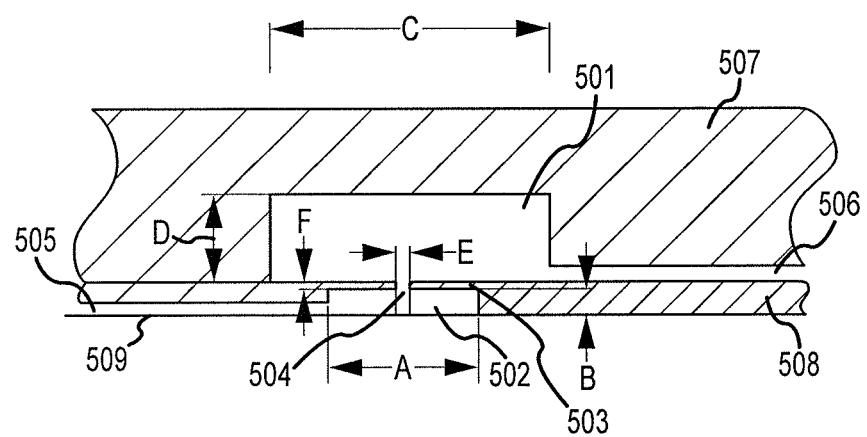
FIG. 6 shows the structure of a microfluidic check valve according to embodiments of the invention.

FIG. 6 shows an exemplary valve. An upper layer (507) defines an outlet chamber (501) that is in fluid communication with and outlet channel (506). The outlet chamber has a height, D, and a chamber width, C. The upper layer is adhered to, pressed onto, or bonded to the membrane (503) with its via (504) opening into the outlet chamber. The membrane has a thickness, F, and a flow channel width (or diameter), E. The membrane layer is adhered to, pressed onto, bonded to, or integral with the bottom layer (508) which defines the input chamber (502) and the input flow channel (505). The input chamber has a width (or diameter), A, and a height, B. The layer 508 is adhered to, pressed onto, or bonded to a substrate (either hard or elastomeric) (509) that forms the inlet channel (505).

In this valve, the footprint of the inlet chamber has an internal width, A, and the inlet chamber has a height, B, the footprint of the outlet chamber has an internal width, C, and the outlet chamber has a height, D. In an embodiment, the membrane channel has a width, E, and a membrane thickness, F. The check valves of the invention will typically have a ratio of C to A is greater than or equal to about 1.2, a ratio of D to B is greater than or equal to about 1.4, and a ratio of A to E is greater than or equal to about 1.9. In further embodiments, the ratio of C to A is equal to or less than about 1.5, equal to or less than about 1.75, equal to or less than about 2, equal to or less that about 2.5, equal to or less than about 3, or greater than 3. The ratio of D to B can be equal to about 1.6 or less, equal to or less than about 1.8, equal to or less than about 2, equal to or less than about 2.5, or equal to or less than about 3, or greater than 3. The ratio of A to E can be equal to or less than about 2.2, equal to or less than about 2.5, equal to or less than about 2.8, equal to or less than about 3, or greater than 3. The membrane thickness, F, can be from about 2 to about 100 um, preferably from about 2 to about 75 um, preferably from about 2 to about 50 um, more preferably from about 2 to about 25 um. In some embodiments, it is preferred that F is less than about 25 um. In some embodiments it is preferred that F is equal to or less than about 10 um. In other embodiments, it is preferred that F is equal to or less than 5 um in thickness. The membrane (503) should have a Young's modulus of about 100 MPA (megapascals) or less. In other embodiments, the Young's modulus of the membrane is about 75 MPA or less, about 50 MPa or less, about 25 MPa or less, about 10 MPa or less, about 8 MPa or less, about 5 MPa or less, or about 2 MPa or less.

The check valve may be used in a device comprising, for example, an inlet channel segment, a check valve, and an outlet channel segment wherein, in the absence of outlet channel flow restrictions, an inlet channel pressure of less than 5 psi (pounds per square inch) is required to produce flow to the outlet channel and wherein substantially no flow occurs from the outlet channel to the inlet channel when an outlet pressure exceeds the inlet channel pressure by about 3 psi. In a further embodiment, the check valve will allow flow to occur from the inlet channel to the outlet channel with an inlet channel pressure of less than 3 psi, 2 psi, 1 psi, 0.5 psi or 0.2 PSI. The initial inlet pressure required to open the check valve will, in some cases, exceed the pressure required to open the check valve in subsequent opening. The opening pressures recited above represent the average opening pressures of 10 repeated openings and closings within a 30 minutes period. In an embodiment, the check valve will close when the pressure in the outlet channel exceeds the pressure in the inlet channel by 2 psi, 1 psi, 0.5 psi, 0.25 psi, 0.1 psi, or 0.05 psi. In a further embodiment, the check valve will close when the pressure in the outlet channel exceeds the pressure in the inlet channel by 0.005 psi.

The check valves are further characterized by a very low dead volume. The check valves my have a dead volume of 100 nL (nanoliters) or less, 50 nL or less, 25 nL or less, 15 nL or less, 10 nL, or less, 5 nL or less, 4 nL or less, 2.5 nL or less, or, in a further embodiment, about 1 nL.

Exemplary Format for the Mixing/Reaction Chamber Array

The microfluidic devices may include sample and reagent wells that are formatted for compatibility with automated reactant loading equipment (e.g., pipetting robots) that already exist and are in common usage in laboratories and manufacturing facilities. The microfluidic devices may also include arrays of mixing/reaction chambers for receiving sample and reagent solutions that are also formatted for compatibility with pre-existing automated sample analysis and/or extraction equipment.

Integrating microfluidic sample delivery technology with high throughput testing equipment combines advantages from both fields. Microfluidic systems have fewer moving parts and simpler operational logistics than robotic fluid delivery systems. In general, the microfluidic systems cost less to manufacture and require less maintenance and repair. In addition, microfluidic systems can be manufactured with smaller sized conduits and chambers, allowing them to deliver smaller volumes of samples, reagents, etc., and with greater precision than practicable with, for example, pipetting robots. This can reduce the costs and waste products generated for large screening studies involving thousands or more combinations of reagents and samples, and improve the accuracy and precision of the results. The small volumes can also make screening and combinatorial studies practical when only a small amount of a sample is available.

Smaller component dimensions also permit more densely packed arrangements of the mixing/reaction chambers. For example, two, four, eight, or more microfluidic reaction chambers (each defining a reaction site) may be packed into the interrogation area of a single site for a standardized high throughput screening device. This can allow the microfluidic device to achieve a twofold, fourfold, eightfold, or more, increase in the throughput rate using an existing screening device.

One widely accepted standard that embodiments of the microfluidic devices may be made compatible with is the SBS format. The Society for Biomolecular Screening ("SBS") has developed formatting standards for microplates used in high throughput screening processes for biological and chemical compounds. These automated processes included the use of robot pipetting to transfer fluid samples to an array of reaction wells formed in the microplate. Detection equipment was aligned with the wells to observe and measure events (e.g., chemical reactions, enzymatic catalysis, crystallizations, etc.). As the number of vendors and systems proliferated, standards were clearly needed to address compatibility problems. SBS developed dimensional standards for microplates that are followed by a significant number of microplate manufacturers and instrument makers that utilize microplates.

SBS has defined dimensional standards for 96, 384, and 1536 well microplates. In each case, the microplate has a rectangular shape that measures 127.76 mm±0.5 mm in length by 85.48 mm±0.5 mm in width. The four corners of the plate are rounded with a corner radius to the outside of 3.18±1.6 mm. The complete definitions for these standards were published by the American National Standards Institute on Mar. 28, 2005, in publications ANSI/SBS 1-2004, ANSI/SBS 2-2004; ANSI/SBS 3-2004; and ANSI/SBS 4-2004, the entire contents of which are herein incorporated by reference for all purposes. A summary of the definitions for 96, 384 and 1536 well plates are provided here:

The 96 Well Format

Figure 7A:
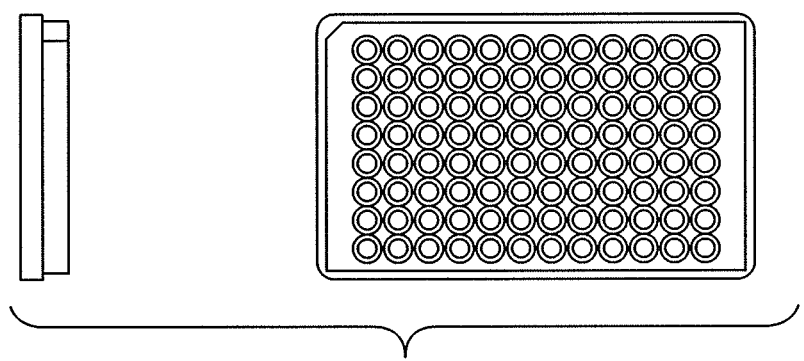
FIGS. 7A-C show schematic views of SBS-formatted microtiter plates for 96, 384 and 1536 reagent wells.

FIG. 7A shows an arrangement for a 96 well microplate, arranged in an 8 row by 12 column rectangular array. The columns of the array are defined by the distance between the left outside edge of the plate and the center of the first column of wells being 14.38 mm. Each additional column is an additional 9 mm in distance from the left outside edge of the plate. The top edge of the part is defined as the two 12.7 mm areas measured from the corners of the plate. The rows of the 96 well array are defined by a distance of 11.24 mm between the top outside edge of the plate and the center of the first row of wells. Each additional row is an additional 9 mm from the top outside edge of the plate. The top edge of the part is defined as the two 12.7 mm areas measured from the corners of the plate.

The 384 Well Format

Figure 7B:
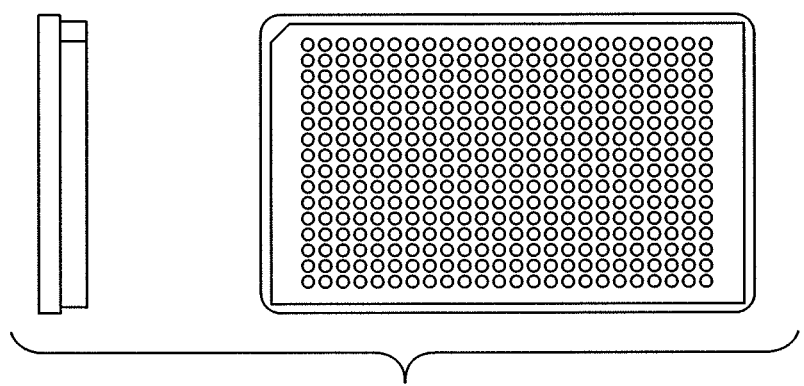

FIG. 7B shows an arrangement for a 384 well microplate, arranged in an 16 row by 24 column rectangular array. The columns of the array are defined by the distance between the left outside edge of the plate and the center of the first column of wells being 12.13 mm. Each additional column is an additional 4.5 mm in distance from the left outside edge of the plate. The top edge of the part is defined as the two 12.7 mm areas measured from the corners of the plate. The rows of the 384 well array are defined by a distance of 8.99 mm between the top outside edge of the plate and the center of the first row of wells. Each additional row is an additional 4.5 mm from the top outside edge of the plate. The top edge of the part is defined as the two 12.7 mm areas measured from the corners of the plate.

The 1536 Well Format

Figure 7C:
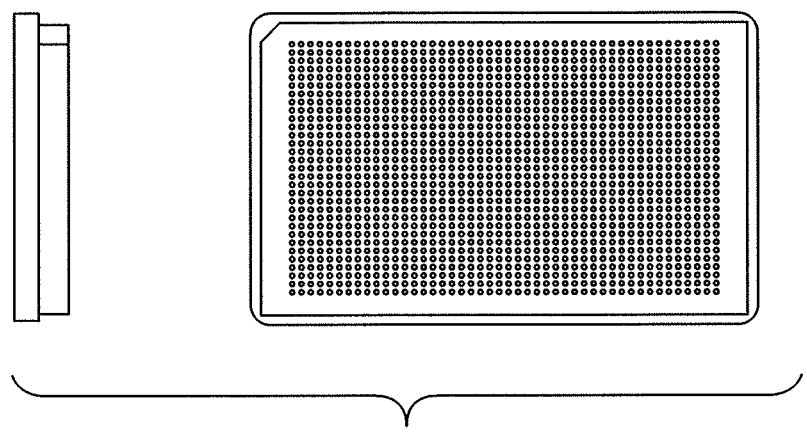

FIG. 7C shows an arrangement for a 1536 well microplate, arranged in an 32 row by 48 column rectangular array. The columns of the array are defined by the distance between the left outside edge of the plate and the center of the first column of wells being 11.005 mm. Each additional column is an additional 2.25 mm in distance from the left outside edge of the plate. The top edge of the part is defined as the two 12.7 mm areas measured from the corners of the plate. The rows of the 1536 well array are defined by a distance of 7.865 mm between the top outside edge of the plate and the center of the first row of wells. Each additional row is an additional 2.25 mm from the top outside edge of the plate. The top edge of the part is defined as the two 12.7 mm areas measured from the corners of the plate.

Utilizing microfluidic devices provided according to embodiments of the present invention, throughput increases are provided over 384 well systems. As an example, throughput increases of a factor of 4, 6, 12, and 24 and greater are provided in some embodiments. These throughput increases are provided while reducing the logistical friction of operations. Moreover the systems and methods of embodiments of the present invention enable multiple assays for multiple samples. For example, in a specific embodiment 24 samples and 24 assays are utilized to provide a total of 576 data points. In another embodiment, 32 samples and 32 assays are utilized to provide a total of 1024 data points. In another embodiment, 48 samples and 48 assays are utilized to provide 2304 data points. In another embodiment, 96 samples and 48 assays are utilized to provide 4608 data points. In another embodiment, 96 samples and 96 assays are utilized to provide a total of 9,216 data points. In a particular example, the 96 assays are components of a TaqMan 5' Nuclease Assay. See, e.g., U.S. Pat. Nos. 5,538,848, 5,723,591, 5,876,930, 6,030,787, 6,258, 569, and 5,804,375, each of which is herein incorporated by reference.

Depending on the geometry of the particular microfluidic device and the size of the microfluidic device and the arrangement of the fluid communication paths and processing site, embodiments of the present invention provide for a range of mixing/reaction chambers. In some embodiments, the methods and systems of the present invention are utilized with chamber densities ranging from about 100 chambers per $cm^2$ to about 1 million chambers per $cm^2$. Merely by way of example, microfluidic devices with chamber densities of 250, 1,000, 2,500, 10,000, 25,000, 100,000, and 250,000 chambers per $cm^2$ are utilized according to embodiments of the present invention. In some embodiments, chamber densities in excess of 1,000,000 chambers per cm² are utilized, although this is not required by the present invention.

Exemplary Structures of Mixing/Reaction Chambers Using "Carry Slug" Technique

Figure 8A:
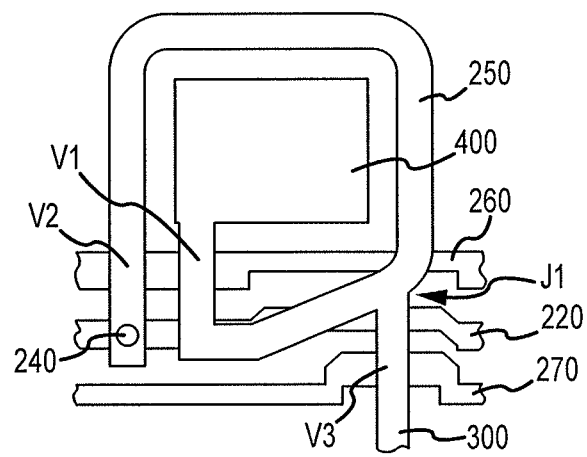
FIGS. 8A-B show schematics of mixing/reaction chambers with carry-slug mixing according to embodiments of the invention.

In embodiments of the invention, the supply and mixing of samples and reagents in the mixing/reaction chamber may be done using a "carry slug" technique. FIG. 8A shows an mixing/reaction chamber unit configured for a carry slug mixing technique. The mixing/reaction chamber 400 may have a variety of shapes (cubical, cylindrical, etc.). Typically the chamber has a volume in the range 1 nL to 1 uL, more often in the range 4 nL to 200 nL. Usually at least one dimension is at least 50 um, and usually at least 100 um.

The mixing/reaction chamber 400 is coupled to a "slug channel" 250. A slug channel is a flow path in fluid communication with the reaction chamber and with a "sample source reservoir" (not shown). Embodiments of the slug channel may include a straight or curved channel in a single level of the device as shown, or it may comprise two or more straight or curved channel segments in different levels of the device connected by one or more linking segments such as a fluid communication via. The slug channel may comprise the shortest path from valve V1 to valve V2. It is sometimes useful to refer to the "slug path" which is a term used to encompass the slug channel along with any fluid communication vias (if present) linking the slug channel to the reaction chamber or linking the slug channel to the sample bus line 220. The slug path may be the shortest flow path from the sample bus line to the reaction chamber, passing through valve V1 and valve V2.

In some embodiments, the slug channel or slug path is the only fluidic channel connected to the reaction chamber (e.g., solutions can enter the reaction chamber only through the slug path). That is, the reaction chamber is a dead-end reaction chamber.

In some embodiments, the slug channel or slug path is the only fluidic channel connected to the reaction chamber (e.g., solutions can enter the reaction chamber only through the slug path). That is, the reaction chamber is a dead-end reaction chamber.

The "first valve" (V1) is situated at the proximal end of the slug channel that, when closed, fluidically isolates the reaction chamber (400) from the more distal part of the slug channel. As used in this context, the term "proximal" refers to a position in the slug path relative to the reaction chamber. An element located in the slug path at a position that is closer to the reaction chamber than the position of a second element is proximal relative to the second element. The second element is distal relative to the first element.

The "second valve" (V2) in the slug channel may be distal to first valve (V1). In some embodiments, the slug path is free of valves in the segment between the first valve (V1) and the second valve (V2).

In general the first and second valves (V1 and V2) are controlled by the same actuation system and are opened or closed at the same time. For example, the valves V1 and V2 may be both controlled by control channel 1 (260). In alternative embodiments, however, the second valve (V2) can be a check valve that prevents flow of solution in the fluidic direction opposite the reaction chamber. That is, solution can flow through valve V2 towards the reaction chamber, but not in the opposite direction.

The slug channel (250) may be in fluid communication with a sample bus line (220) at a junction distal to the second valve (V2). A sample bus line is a flow channel in fluid communication with a sample source reservoir and with slug paths of a plurality of unit cells (e.g., a row of unit cells). Usually the plurality comprises at least 10 unit cells, often at least 30 unit cells, often at least 40 unit cells, and sometimes at least 96 unit cells. In some embodiments the plurality is exactly 32, 48, or 96 unit cells. Each unit cell is in fluid communication with a single sample bus line. In some embodiments, unit cells of each row in an array are fluidically connected to a different sample bus line. Thus, in some embodiments the sample bus line constitutes a fill source for the slug paths of a particular row. Using this arrangement the slug path of cells of each row will be loaded with the same sample.

The sample bus line (220) may be connected to the slug channel distal to the second valve by a fluid communication via (240), or other linking segment and/or by a "sample input line" (290) (see, e.g., FIG. 6). The sample input line 290 may be short.

As will be apparent, closure of the second valve (V2) prevents flow from the sample bus line (or sample input line) to the reaction chamber.

In certain embodiments the slug channel is in fluid communication with a reagent bus line (230). A reagent bus line is a bus line in fluid communication with a reagent source and with slug channels of a plurality of unit cells (e.g., a row of unit cells). Usually the plurality comprises at least 10 unit cells, often at least 30 unit cells, often at least 40 unit cells, and sometimes at least 96 unit cells. In some embodiments the plurality is exactly 32, 48, or 96 unit cells. Each unit cell is in fluid communication with a single reagent bus line. In some embodiments, unit cells of each column in an array are fluidically connected to a different reagent bus line.

A reagent input channel (300) may be in fluid communication with the slug channel at a junction (J1) that lies between the first valve (V1) and second valve (V2) (i.e., is distal to valve V1 and proximal to valve V2). The reagent input channel is in fluid communication with a reagent source reservoir. With valves V1 and V2 closed, reagent solution can flow from the reagent source reservoir into the slug channel, filling the portion of the slug channel between valves V1 and V2 with solution.

In some embodiments the reagent input channel is linked to the reagent source reservoir though a reagent bus line (230). In some embodiments the reagent input channel comprises or consists of a fluid communication via, or other linking segment through which reagent solution flows from the reagent bus line.

In some embodiments, the slug channel is not fluidically connected in the segment between the first valve (V1) and second valve (V2) to any input lines other than the reagent input channel. That is, junction J1 is the only junction in this segment.

In alternate embodiments (not shown) a distinct reagent bus line is not used, but instead a reagent input channel (300) of each cell is linked to the slug channel of an adjacent cell in the slug channel segment bounded by the first and second valves (V1 and V2). When valves V1 and V2 are closed reagent introduced into one reagent input channel flows to all reagent input channels in a row. In some such embodiments, exactly two reagent input channels (one corresponding to the cell and one corresponding to an adjacent cell) are the only channels in fluid communication with the slug path in the region of the slug path lying between valves V1 and V2.

It will be clear that other arrangements and architectures, with or without bus lines may be used, so long as a reagent solution from a single reagent source can be delivered to slug channels of a plurality of unit cells in the slug channel segments that lie between valve V1 and valve V2.

Each unit cell may also comprises a "third valve" (V3) that regulates flow from the reagent input channel to the slug channel of each cell in a column. The position of the third valve will depend on the nature of the reagent input channels and reagent bus line (if present). The third valves may be located in each reagent input line. Alternatively the third valves may be located in the reagent bus line between cells. When the third valves of a column of unit cells are closed, each unit is fluidically isolated from other cells in the same column, but remain fluidically connected through a sample bus line to other cells in the row. In this embodiment the slug channels of a given column are therefore interconnected when valve 3 is open, but capable of being isolated from each other upon actuation of control channel 2 (270).

Alternatively, the third valve (V3) may be a check valve that permits fluid flow toward the unit cell reaction chamber, but does not permit flow through the valve in the reverse direction.

In some embodiments, in a microfluidic device sample flowing from the sample bus line to the reaction chamber passes though exactly two, no more than three (e.g., exactly three), or no more than four (e.g., exactly four) valves. In some embodiments, sample flowing from the sample bus line to the reaction chamber passes though exactly one check valve, or through exactly two check valves. In some embodiments, sample flowing from the sample bus line to the reaction chamber passes though exactly two valves, one of which is a check valve, or exactly three valves, one or two of which is a check valve.

Embodiments of the microfluidic devices may comprise reagent source reservoirs and sample source reservoirs which are part of an integrated carrier device. Source reservoirs may include containers, wells, chambers and the like that can be loaded with desired sample and reagent solutions. The microfluidic devices may comprise reagent source reservoirs and sample source reservoirs which are part of an integrated carrier device. Alternatively, channels of the device can be fluidically connected to external reservoirs. Generally each sample bus line (220) is in fluid communication with a sample source reservoir (which is usually a unique reservoir) and each reagent bus line is in fluid communication with a reagent source reservoir (which is usually a unique reservoir). In embodiments of microfluidic devices designed without each reagent bus lines, reagent input channels of each column may be fluidically connected to a reagent source reservoir. The source reservoirs are generally not filled with solutions until they are being prepared for use. However, in some embodiments devices are provided in which at least some reservoirs are prefilled.

In microfluidic devices using integrated elastomeric on-off valves, each cell may also comprise a portion of at least one control channel. Typically the device includes a "first control channel" (260), which regulates flow through the first valve V1 and the second valve V2, and a "second control channel" (270), which regulates flow through the third flow channel V3. The valves are opened or closed in response to pneumatic or hydraulic pressure in a control channel, causing deflectable membrane portions to deflect into the flow channels to stop flow of solution through a flow channel and fluidically separate regions of a flow channel from each other. Usually the control channels are located in a layer of the device that is adjacent to the layer containing the regulated flow channel. In a preferred embodiment each cell comprises portions of two control channels, a first control channel (260) regulating valves V1 and V2, and a second control channel (270) regulating valve V3. In an alternative embodiment valves V1 and V2 can be controlled by two different control channels. In embodiments in which valve V3 is a one-way check valve, it is possible to omit control channel 2.

In one embodiment each first control channel regulates valves V1 and V2 along a row of the array, and each second control channel regulated valves V3 along a column of the array.

Figure 8B:
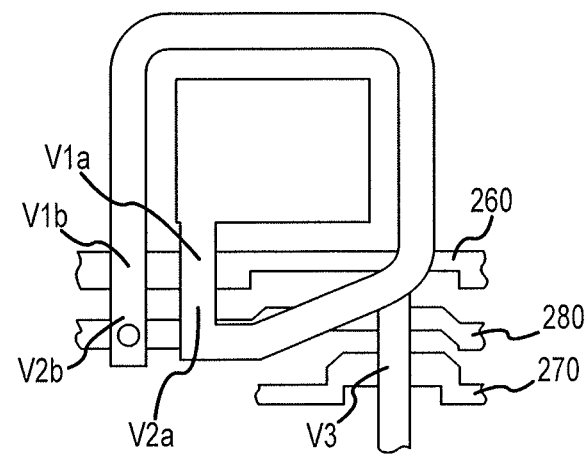

FIG. 8B shows another embodiment of an mixing/reaction chamber unit configured for a carry slug mixing technique. In this embodiment, the control channel 280 is called a "latch" and is operable to actuate the closure of valves V2a and V2b, which are in series. Thus, if either V2a or V2b, or both, are closed, the valve V2 is considered closed. Control channel is called an "interface" and is operable to actuate the closure of valves V1a and V1b, which are also in series. Thus, if either valve V1a or V1b is closed, the valve V1 is considered closed. The control channels 260 and 280 act in unison on all valves serially connected to each channel. The control channel 270 is called a "containment" line.

One difference between control channel 260 (the interface line) and control channel 280 (the latch line) is the type of valve used to pressurize the channels. For control channel 280 a check valve is incorporated into the channel upstream of any branching that keeps the channel 280 irreversibly pressurized. For control channel 260 a reversible flow microfluidic valve is incorporated in the upstream position to allow V1 (i.e., valves V1a and V1b) to be reversibly asserted and deasserted.

IV. Exemplary Operation of the Microfluidic Devices

Carry Slug Mixing of Samples and Reagents

As noted above, one technique for concurrently filling and mixing samples and reagents in the mixing/reaction chambers according to embodiments of the invention is the "carry slug" technique. Embodiments of this technique may include filling a slug path (e.g., by blind filling) with a reagent solution. The reagent is contained in a section of the slug path bounded by valves V1 and V2 shown in FIG. 8 above. A sample solution is introduced through the sample bus line (and optionally through a sample input channel), typically by blind filling, into the section of the slug path distal to valve V2. Valves V1 and V2 is then opened and the sample solution is forced through the slug path such that it pushes the reagent solution through the slug path into the reaction chamber. Typically the reaction chamber is filled by blind filling. As noted above, the volume of reaction chamber exceeds the volume of reagent solution forced into the chamber, with the result that both reagent and sample solutions are introduced into the chamber. It has been discovered by the inventors that this process results in highly efficient mixing of the reagent and sample solutions. It has also been determined that assays carried out using the microfluidic device resulted in surprisingly superior results compared to use of prior art devices under the same conditions. See, e.g., U.S. patent application Ser. No. 12/018,138, filed Jan. 22, 2008, entitled "HIGH EFFICIENCY AND HIGH PRECISION MICROFLUIDIC DEVICES AND METHODS", the entire contents of which is herein incorporated by reference for all purposes.

Efficiency in mixing for two solutions can be measured. For a first solution containing solute A and a second solution containing solute B, can be measured as the amount of B dispersed in the first solution at a given period of time. For miscible solutions, the mixing will be 100% efficient over a long enough period of time. Efficiency can be measured by art known methods. In one assay, mixing efficiency is assayed using TaqMan Gene Expression Assays as an indicator. The assay includes a FAM™ dye labeled TaqMan® MGB (minor groove binder) probe. The probe has been generally used as a quantification reporter in real time PCR. Fluorescence intensity in a microfluidic chamber corresponds to the presence of the probe. In determining mixing efficiency, two solutions are used. A first solution does not contain probe. A second solution contains 2 µM probe. The solutions are loaded into a microfluidic device and chamber loading initiated. Upon completion of loading the chamber(s) with the solutions, a fluorescent intensity image is taken by a high resolution fluorescence camera. That image is compared with a standard fluorescence image. The standard image is obtained by mixing the first solution with the second solution before loading the microfluidic system and then loading the mixture into the microfluidic device. The mixing efficiency is defined as the fluorescence intensity of the on-device mixed solutions divided by the intensity of the standard image intensity. Using the devices and methods of the present invention, mixing occurs more rapidly than prior art devices. In one embodiment, twenty five percent (25%) efficiency is achieved in 30 minutes or less, often less than 20 minutes, often less than 10 minutes, often less than 5 minutes, and sometimes less than 1 minute. In one embodiment, fifty percent (50%) efficiency is achieved in 30 minutes or less, often less than 20 minutes, often less than 10 minutes, often less than 5 minutes, and sometimes less than 1 minute. In one embodiment, seventy five percent (75%) efficiency is achieved in 30 minutes or less, often less than 20 minutes, often less than 10 minutes, often less than 5 minutes, and sometimes less than 1 minute.

Without intending to be bound by a particular mechanism, it is believed the superior results are a consequence of improved and highly efficient mixing of solutions achieved by the devices disclosed herein. Indeed, the mixing of the solutions is typically greater that 25% efficient, preferably greater than 35% efficient, more preferably greater than 50% efficient, more preferably greater that 65% efficient, more preferably greater than 75% efficient, more preferably greater than 85% efficient, more preferably greater than 90% efficient, more preferably greater than 95% efficient, more preferably greater than 99% efficient, and more preferably about 100% efficient.

The volume of reagent displaced into the reaction chamber is determined primarily by the dimensions of the slug path and position of valves V1 and V2. In general the volume of reagent introduced into the reaction chamber corresponds to the volume of the slug path lying between valves V1 and V2, referred to as the "slug volume" (SV). The actual volume of reagent introduced into the reaction chamber can be varied upward, if desired, based on design and process conditions. The careful reader will have noted that the volume defined in each cell when valves V1, V2 and V3 of an array are closed exceeds the slug volume. If during the operation of the device the sample solution was forced through the slug channel relatively slowly, a portion of the reagent solution in the "non-flowing volume" NFV would diffuse into the reagent or sample solution flowing past, increasing the amount of reagent introduced into the reaction chamber. In practice, because flow through microfluidic channels is primarily laminar the amount of solution that diffuses from the NFV into the flow path will usually be minor under conditions of normal use. Channel sizes, aspect ratios, and orientations, along with the speed of flow of reagent and sample solutions through the slug path, can be adjusted to minimize, or if desired increase, the amount of NFV content that enters the reaction chamber.

In some embodiments, more than one reagent solution may be introduced along with sample into mixing/reaction chambers.

The operation of an exemplary microfluidic device configured for a carry slug mixing technique is illustrated in FIGS. 9A-H. The illustrations in these figures are somewhat idealized in that they show all of the reagent solution entering the reaction chamber before any of the sample solution enters. In practice, due to sheath flow, a bullet-shaped flow velocity profile will occur in the slug channel segment. Therefore, to achieve complete transfer of the reagent solution from the slug path into the reaction chamber, it is desirable that the reaction chamber volume be at least 2 times that of the slug volume (volume of solution 1 introduced into the chamber). Preferably the reaction chamber volume is at least 3 times the slug volume, more preferably at least 4 times, often at least 5 times, at least 6 times, at least 7 times, at least 8 times, or at least 9 times the slug volume.

Figure 9A:
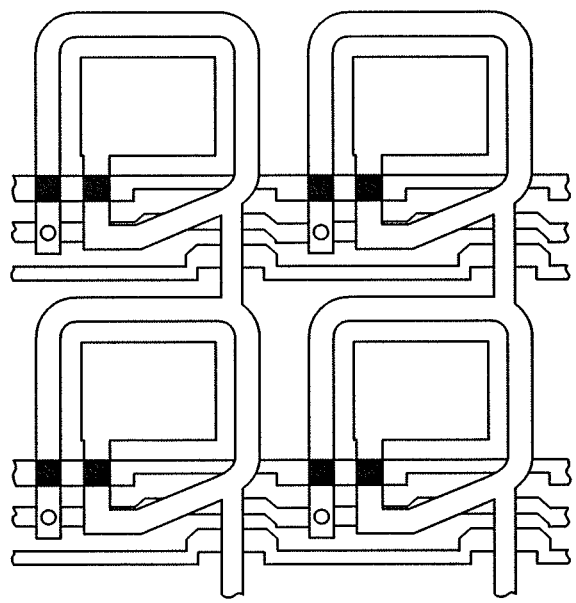
FIGS. 9A-H are illustrations of stages in filling mixing/reaction chambers using carry-slug mixing according to embodiments of the invention.

FIG. 9A: Control channel 1 (260) is pressurized to close the valves that fluidically isolate the ends of the slug channel segment (valves V1 and V2).

Figure 9B:
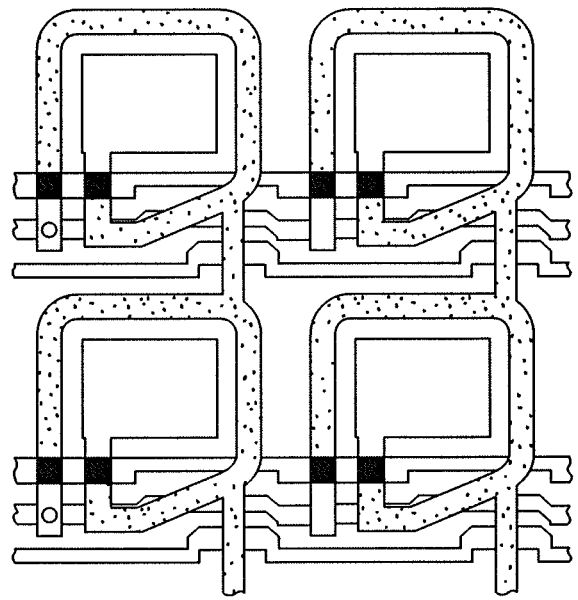

FIG. 9B: A reagent solution (solid dots) is introduced under pressure through the reagent input channels (300), through open valve 3 (V3), and the slug channels are blind-filled.

Figure 9C:
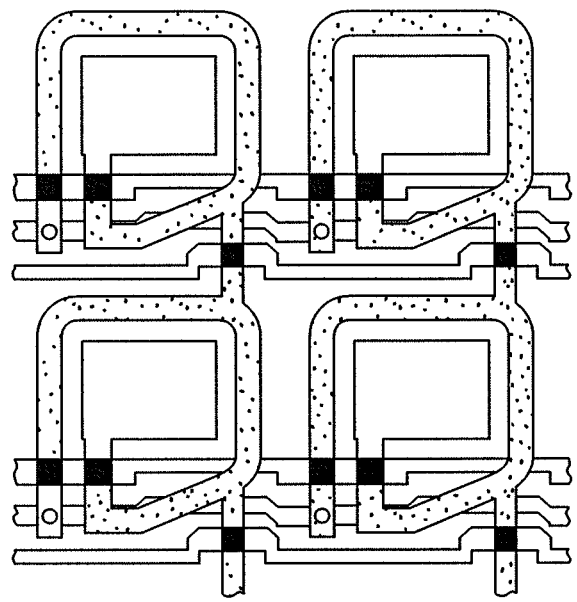

FIG. 9C: Following the filling of the slug channels, control channel 2 (270) is pressurized to actuate the valves (V3) that close off the reagent input channels (300) and thereby isolate the individual slug channels from the other slug channels in the columns. In arrays in which there is a reagent bus line valve V3 can be located in the bus line between cells, or in the reagent input channel associated with each cell.

Figure 9D:
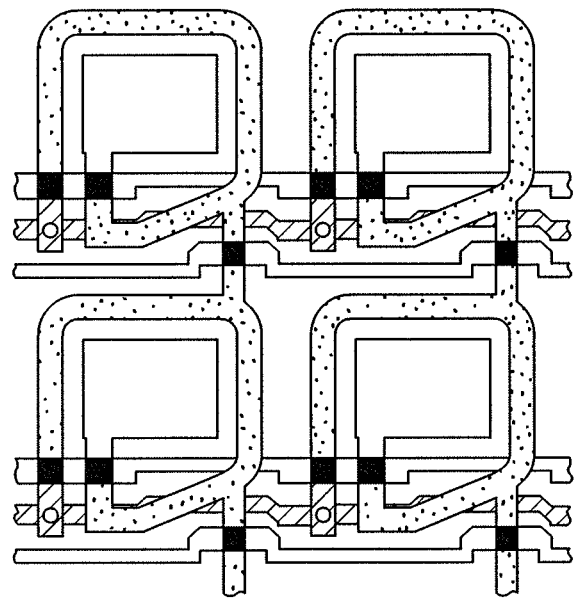

FIG. 9D: Following the blind filling of the slug channels and their isolation, a sample solution (open dots) is introduced under pressure into each sample bus line (220). Although for clarity FIG. 9 shows sequential addition of reagent and sample, it is also possible, and often preferred, to inject reagent and sample at the same time, with valves V1 and V2 closed and valve V3 open.

Figure 9E:
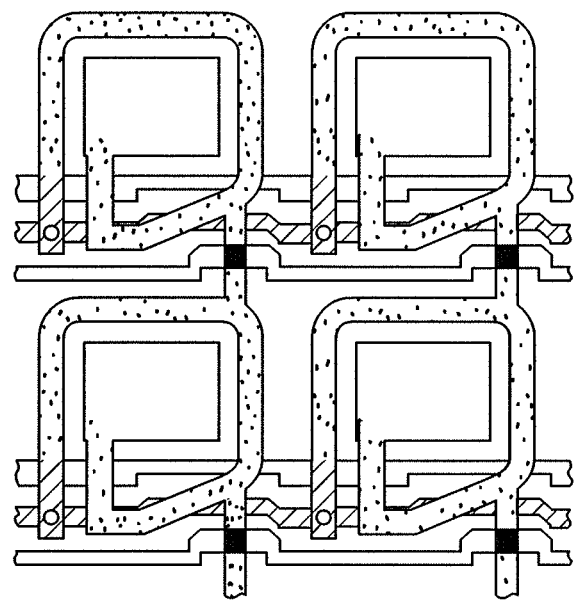
Figure 9F:
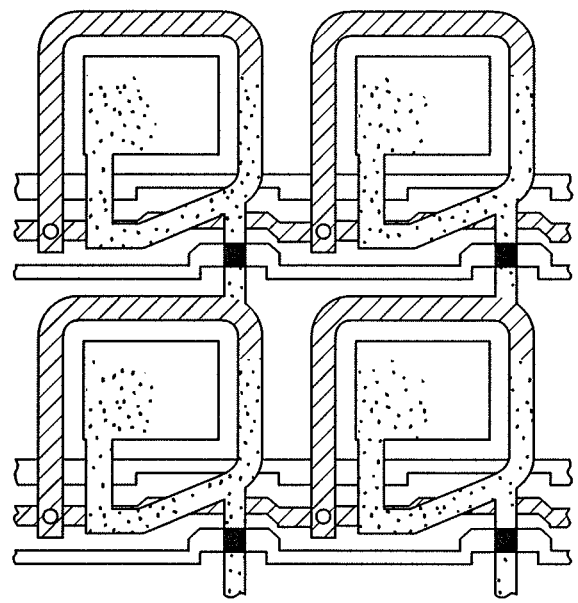

FIGS. 9E and 9F: The control channels 1 (260) are then depressurized to open the interface valves (V1 and V2) that were previously closed to isolate the ends of the slug channels. The sample solution enters the slug channel at the first end and pushes the reagent into the reaction chamber. The conditions of the sample injection will vary. In some embodiments the sample solution is injected under pressure in the range 8-15 psi.

Figure 9G:
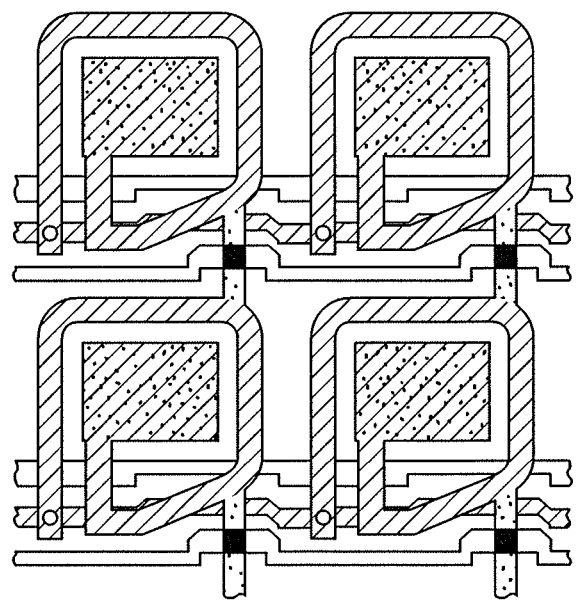

FIG. 9G: This results in a highly mixed, loaded reaction chamber (400) containing the 5 nL of reagent solution and 45 nL of sample solution (50 nL total reaction chamber volume).

Figure 9H:
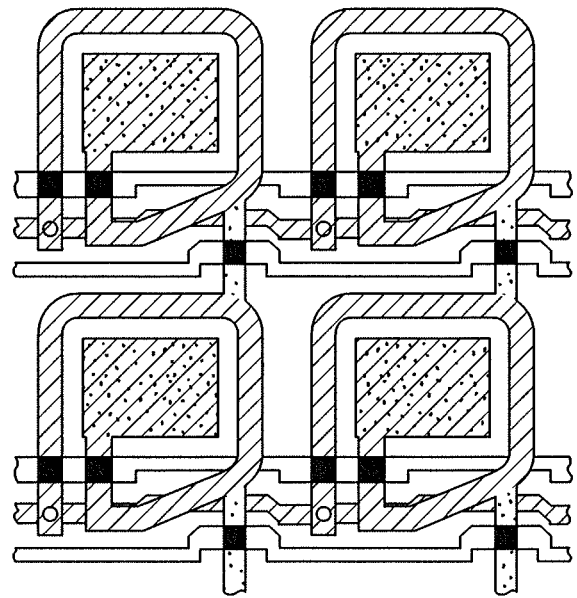

FIG. 9H: Finally, in this demonstration, control channel 1 is pressurized which results in the closure of the interface valves.

Although all rows in the reaction array, and accordingly all sample input channels in a given column, are filled with the same sample solution, there is no interconnection between the sample input channels of the individual columns and different samples can be introduced into the individual columns. For example, in a 32×32 matrix, 32 separate samples can be simultaneously mixed and loaded into reaction chambers with 32 separate reagents for 1024 individual experiments.

Although generally discussed in term of mixing of solutions, more generally the invention provides a method of combining two solutions in a microfluidic chamber. For example, the invention provides a method for combining two solutions in a microfluidic reaction chamber by introducing a predetermined volume of a first solution into a reaction chamber, introducing a predetermined volume of a second solution into a reaction chamber, and fluidically isolating the reaction chamber. Advantageously, the microfluidic methods and devices result in introduction of essentially all of the first solution (and a defined volume of the second solution) into a chamber. Following introduction into the chamber rapid mixing may occur due to an increased interface, as discussed above, and because, for a solute in solution 1 the average diffusional path length to solution 2 is shorter than in prior art microfluidic devices (and, equivalently, for a solute in solution 2 the average diffusional path length to solution 1 is shorter than in prior art microfluidic devices). Thus, predetermined amounts of two solutions can be introduced into a chamber. The chamber can then be fluidically isolated.

Moreover, using methods described herein more than two solutions can be introduced into a chamber by sequentially introducing predetermined volumes of N different solutions where N is at least 2. Usually N is from 2 to 10, usually 2-5, such as 2, 3, 4 or 5. The combined total volume of the solutions is about equal to the fluid capacity of the reaction chamber.

Figure 10:
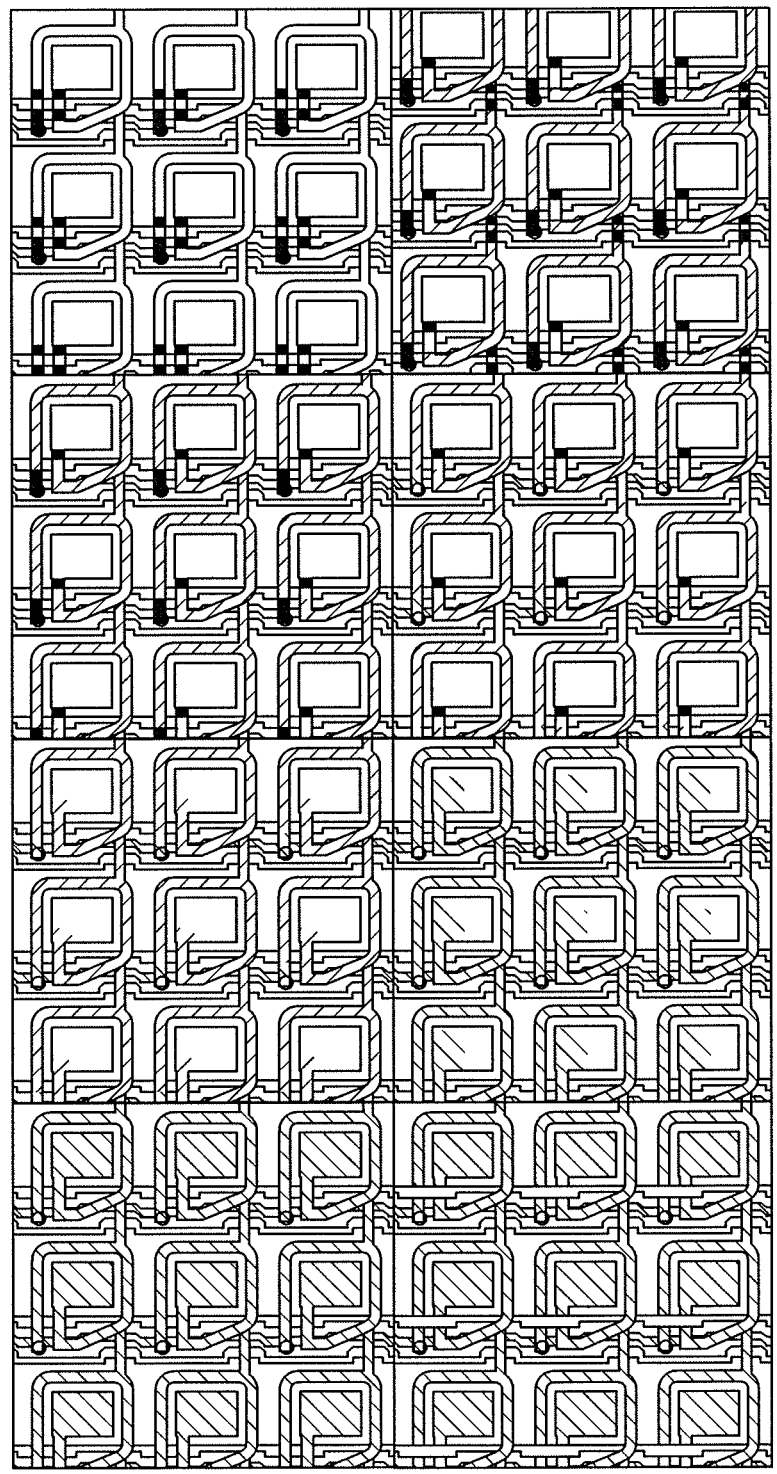
FIG. 10 shows snapshots of stages in filling a 3×3 array of mixing/reaction chambers using carry-slug mixing according to embodiments of the invention.

FIG. 10 shows snapshots of stages ("a" through "h") in filling a 3×3 array of mixing/reaction chambers using carry-slug mixing according to embodiments of the invention. Each of the 9 mixing/reacting chamber units includes a 50 nL chamber, a 5 nL reagent chamber, a horizontal sample line, and two controlled lines located in a different layer. The sample lines get connected with the flow channel through a laser punched via. As depicted in stage "a", valve 1 was pressurized and the device was ready to load. After the primer-probe reagent was loaded from a vertical direction, the reagent chamber was fully filled and restricted at two ends with valve 1 (see stage "b"). Valve 2 was then closed (stage "c"), separating the reagents between different rows. The sample solution in the horizontal direction was then pushed into the device. When valve 1 was depressurized, the reagent was released into the mixing/reaction chamber because of the pressure from the sample solution (stage "e"). The sample solution was then pushed further, carrying the reagent liquid into the reaction chamber (stage "f"). The reagent chamber height was 30 µm, about 20 µm higher than the flow channel. Since the mixing character distance was about 10 µm, the diffusion time scale was about 30 seconds. Because the loading time was controlled between 10 to 20 minutes, the diffusion dominated the mixing occurring in the reagent channel before it entered the mixing/reacting chamber. When the loading of the chamber was finished, the mixing appeared rapid, uniform and thorough (see stage "g"). After the loading, valve 1 was closed and the PCR cocktail was ready for PCR thermal cycling (stage "h").

Exemplary Operation of Microfluidic Check Valve

Figure 11A:
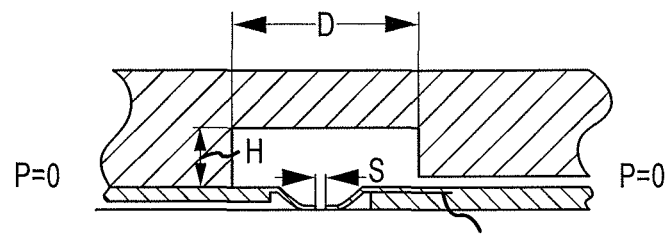
FIGS. 11A-D show illustrations of stages in flowing fluid through a microfluidic check valve according to embodiments of the invention.
Figure 11B:
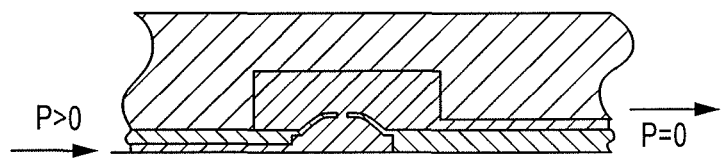
Figure 11C:
Figure 11D:
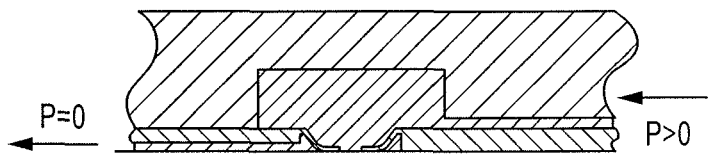

FIGS. 11A-D depict the functional process for a normally closed microfluidic check valve. At its original normally closed state (FIG. 11A), the membrane with a pore is relaxed and the portion of the membrane containing the pore rests on the floor of the bottom chamber. The valve is closed do to the portion of the membrane surrounding the pore touching the substrate and thereby sealing the bottom chamber. When a forward pressure is applied (FIG. 11B), the membrane is raised by the flowing liquid which then passes through the membrane pore. When the forward pressure ceases and both the top and bottom chambers are filled with liquid, the membrane returns to the normally close state (FIG. 11C). When reverse pressure is applied, the liquid in the top chamber exerts a pressure on the membrane and the channel is closed (FIG. 11D). There is substantially no back flow under this condition.

V. Systems

The microfluidic devices described herein may be used in conjunction with additional elements including components external to the device. Examples of external components include external sensors, external chromatography columns, actuators (e.g., pumps or syringes), control systems for actuating valves, data storage systems, reagent storage units (reservoirs), detection and analysis devices (e.g., a mass spectrophotometer), programmable readers, controllers, and other components known in the art. See, e.g., co-pending and commonly owned U.S. Patent Publication Nos. 2006/0006067, 2007/0074972; 2005/0214173; and 2005/0118073 each of which is incorporated herein for all purposes.

The microfluidic devices utilized in embodiments of the present invention may be further integrated into the carrier devices such as, for example, those described in co-pending and commonly owned U.S. Patent Application No. US2005/0214173A1, incorporated herein for all purposes. These carriers may help maintain fluid pressure to maintain valve closure away from a source of fluid pressure, e.g., house air pressure. Further provided is an automated system for charging and actuating the valves of the present invention as described therein. An another preferred embodiment, the automated system for charging accumulators and actuating valves employs a device having a platen that mates against one or more surfaces of the microfluidic device, wherein the platen has at least two or more ports in fluid communication with a controlled vacuum or pressure source, and may include mechanical portions for manipulating portions of the microfluidic device, for example, but not limited to, check valves.

Another device utilized in embodiments of the present invention provides a carrier used as a substrate for stabilizing an elastomeric block. Preferably the carrier has one or more of the following features; a well or reservoir in fluid communication with the elastomeric block through at least one channel formed in or with the carrier; an accumulator in fluid communication with the elastomeric block through at least one channel formed in or with the carrier; and, a fluid port in fluid communication with the elastomeric block, wherein the fluid port is preferably accessible to an automated source of vacuum or pressure, such as the automated system described above, wherein the automated source further comprises a platen having a port that mates with the fluid port to form an isolated fluid connection between the automated system for applying fluid pressure or vacuum to the elastomeric block. In devices utilized in certain embodiments, the automated source can also make fluid communication with one or more accumulators associated with the carrier for charging and discharging pressure maintained in an accumulator.

In certain embodiments, the carrier may further comprise a region located in an area of the carrier that contacts the microfluidic device, wherein the region is made from a material different from another portion of the carrier, the material of the region being selected for improved thermal conduction and distribution properties that are different from the other portion of the carrier. Preferred materials for improved thermal conduction and distribution include, but are not limited to silicon, preferably silicon that is highly polished, such as the type of silicon available in the semiconductor field as a polished wafer or a portion cut from the wafer, e.g., chip.

Embodiments of the present invention utilize a thermal source, for example, but not limited to a PCR thermocycler, which may have been modified from its original manufactured state. Generally the thermal source has a thermally regulated portion that can mate with a portion of the carrier, preferably the thermal conduction and distribution portion of the carrier, for providing thermal control to the elastomeric block through the thermal conduction and distribution portion of the carrier. Embodiments include improving the thermal contact by applying a source of vacuum to a one or more channels formed within the thermally regulated portion of the thermal source, wherein the channels are formed to contact a surface of the thermal conduction and distribution portion of the carrier to apply suction to and maintain the position of the thermal conduction and distribution portion of the carrier.

In some embodiments, the thermal conduction and distribution portion of the carrier may not be in physical contact with the remainder of the carrier, but is associated with the remainder of the carrier and the elastomeric block by affixing the thermal conduction and distribution portion to the elastomeric block only and leaving a gap surrounding the edges of the thermal conduction and distribution portion to reduce parasitic thermal effects caused by the carrier. It should be understood that in many aspects of the invention described herein, the preferred elastomeric block could be replaced with any of the known microfluidic devices in the art not described herein, for example devices produced such as the GeneChip® by Affymetrix® of Santa Clara, Calif., USA, or by Caliper of Mountain View, Calif., USA. U.S. patents issued to Soane, Parce, Fodor, Wilding, Ekstrom, Quake, or Unger, describe microfluidic or mesoscale fluidic devices that can be configured to utilize the carry slug mixing methods or devices of the current invention. A unit cell of the invention can be used as a mixing module in a microfluidic device containing other elements. In such an embodiment the reagent input channel 300 and/or sample input channel 290 may be linked to a solution reservoir or, alternatively, to a channel that is an output of a different on-chip element such as a column, chamber, or channel. Similarly, the reaction chamber may include an exit channel (500) that fluidically connected to a different on-chip element such as a column, chamber, or channel. Examples include microfluidic protein crystallization devices, bioprocessing devices including cell-based assay devices, microfluidic immunoassay devices, combinatorial synthesis systems, nucleic acid sample preparation devices, electrophoretic analytical devices, microfluidic microarray devices, microfluidic devices incorporating electronic or optical sensors, and nucleic acid and protein sequencing devices.

VI. Exemplary Characteristics and Fabrications of Microfluidic Devices

Figure 12A:
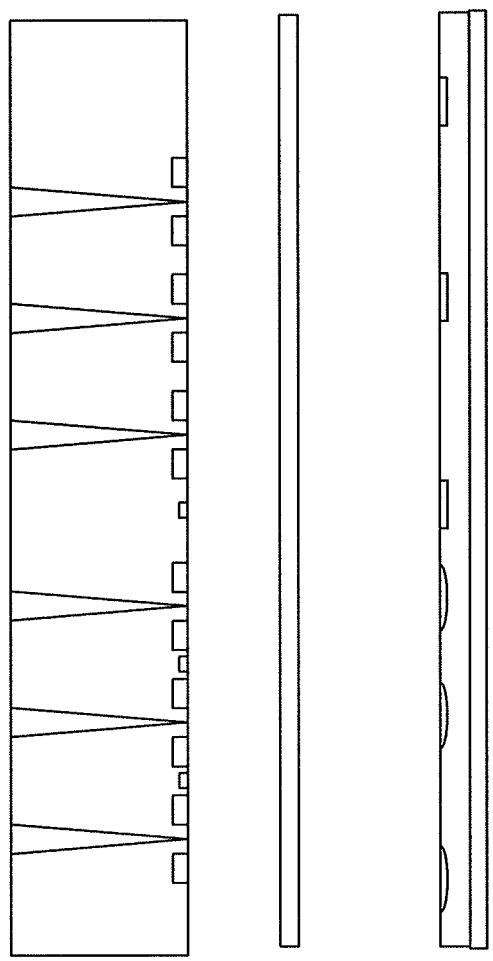
FIGS. 12A and B show exploded views of layers of a microfluidic device during fabrication according to two different embodiments of the invention.

FIGS. 12A and B show exploded views of layers of a microfluidic device during fabrication according to embodiments of the invention. As shown in FIG. 12A, these layers include an injection molded rigid plastic top layer made from a cyclo-olefin polymer ("COP") such as Zeonor® made by Zeon Corp of Tokyo Japan. In the embodiment shown, the rigid plastic top layer is a single injected molded plastic layer that includes structures for both conical-shaped wells that extend through the thickness of the layer, and recesses for mixing/reaction chambers and fluid and/or control channels formed in the surface of the layer that contacts the underlying elastomeric portion of the device.

The elastomeric portion in the embodiment shown is made from two elastomeric layers. The upper elastomeric layer is a 10 μm layer made from PDMS that has vias for fluid communication between the rigid plastic top layer and the underlying elastomeric layer. The lower elastomeric layer includes structures for channels and valves and may also be made from PDMS. Both of these layers may be fabricated by spin coating the PDMS on a mold having raised features for the structures formed in the elastomeric layer.

The elastomeric portion of the device rests on a rigid base layer that may be constructed from the same rigid plastic as the rigid plastic top layer. Alternatively, the base layer may be constructed from a different material such including other plastics, ceramics, and/or metals. In the embodiment shown in FIGS. 12A and B, the rigid plastic base layer is a 200 μm urethane layer.

Figure 12B:
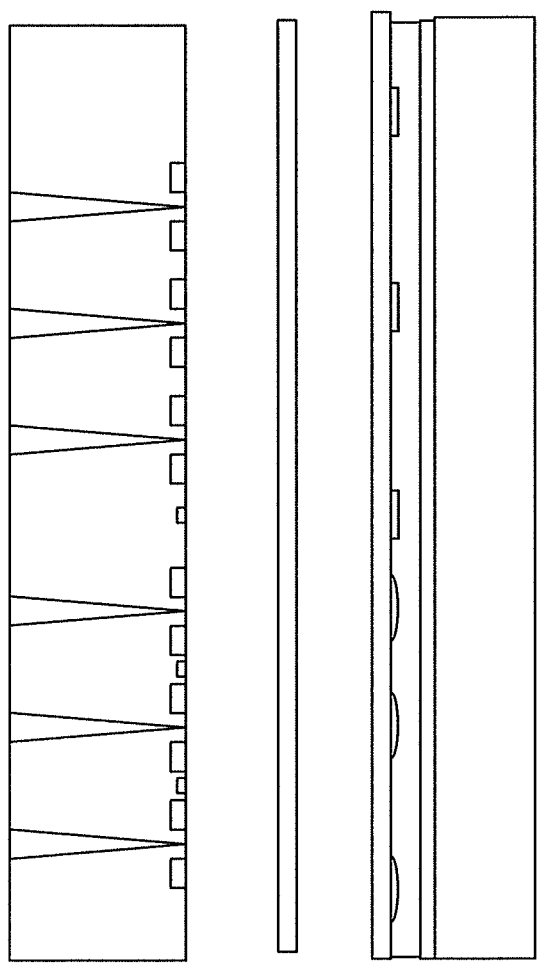

FIG. 12B outline some of the steps that may be used to construct the microfluidic device shown. These steps include: 1. Providing an epoxy hard mold, and 2. spinning a 35 μm PDMS layer on the mold. The steps also include: 3. Spinning the 200 μm urethane layer and 4. Pouring a sacrificial layer before 5. demolding. The steps may further include 6. pouring PDMS onto a flat wafer, 7. spinning the 10 μm PDMS layer, 8. bonding, 9. Demolding, 10. laser punching the vias, 11. bonding to the carrier, and 12. removing the sacrificial layer.

Microfluidic devices can be constructed out of any material or combination of materials that can be fabricated to have microfluidic channels and chambers, and valves that regulate flow through channels and into chambers. Materials from which a device can be fabricated include, without limitation, elastomers, silicon, glass, metal, polymer, ceramic, inorganic materials, and/or combinations of these materials.

The methods used in fabrication of a microfluidic device will vary with the materials used, and include soft lithography methods, microassembly, bulk micromachining methods, surface micro-machining methods, standard lithographic methods, wet etching, reactive ion etching, plasma etching, stereolithography and laser chemical three-dimensional writing methods, modular assembly methods, replica molding methods, injection molding methods, hot molding methods, laser ablation methods, combinations of methods, and other methods known in the art or developed in the future. A variety of exemplary fabrication methods are described in Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rossier et al., 2002, "Plasma etched polymer microelectrochemical systems" *Lab Chip* 2:145-150; Becker et al., 2002, "Polymer microfluidic devices" *Talanta* 56:267-287; Becker et al., 2000, "Polymer microfabrication methods for microfluidic analytical applications" *Electrophoresis* 21:12-26; U.S. Pat. No. 6,767,706 B2, e.g., Section 6.8 "Microfabrication of a Silicon Device"; Terry et al., 1979, A Gas Chromatography Air Analyzer Fabricated on a Silicon Wafer, *IEEE Trans. on Electron Devices*, v. ED-26, pp. 1880-1886; Berg et al., 1994, *Micro Total Analysis Systems*, New York, Kluwer; Webster et al., 1996, *Monolithic Capillary Gel Electrophoresis Stage with On-Chip Detector* in International Conference On Micro Electromechanical Systems, *MEMS* 96, pp. 491496; and Mastrangelo et al., 1989, *Vacuum-Sealed Silicon Micromachined Incandescent Light Source*, in Intl. Electron Devices Meeting, IDEM 89, pp. 503-506.

A) Elastomeric Fabrication

Embodiments include one or more layers of the device being fabricated from elastomeric materials. Fabrication methods using elastomeric materials and methods for design of devices and their components have been described in detail in the scientific can patent literature. See, e.g., Unger et al., 2000, *Science* 288:113-16; U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic systems including three-dimensionally arrayed channel networks); U.S. Patent Application publication Nos. 2004/0115838, 20050072946; 20050000900; 20020127736; 20020109114; 20040115838; 20030138829; 20020164816; 20020127736; and 20020109114; PCT patent publications WO 2005/084191; WO05030822A2; and WO 01/01025; Quake & Scherer, 2000, "From micro to nanofabrication with soft materials" Science 290: 1536-40; Xia et al., 1998, "Soft lithography" Angewandte Chemie-International Edition 37:551-575; Unger et al., 2000, "Monolithic microfabricated valves and pumps by multilayer soft lithography" *Science* 288:113-116; Thorsen et al., 2002, "Microfluidic large-scale integration" *Science* 298:580-584; Chou et al., 2000, "Microfabricated Rotary Pump" Biomedical Microdevices 3:323-330; Liu et al., 2003, "Solving the "world-to-chip" interface problem with a microfluidic matrix" *Analytical Chemistry* 75, 4718-23," Hong et al, 2004, "A nanoliter-scale nucleic acid processor with parallel architecture" *Nature Biotechnology* 22:435-39; Fiorini and Chiu, 2005, "Disposable microfluidic devices: fabrication, function, and application" *Biotechniques* 38:429-46; Beebe et al., 2000, "Microfluidic tectonics: a comprehensive construction platform for microfluidic systems." *Proc. Natl. Acad. Sci. USA* 97:13488-13493; Rolland et al., 2004, "Solvent-resistant photocurable "liquid Teflon" for microfluidic device fabrication" *J. Amer. Chem. Soc.* 126:2322-2323; Rossier et al., 2002, "Plasma etched polymer microelectrochemical systems" *Lab Chip* 2:145-150; Becker et al., 2002, "Polymer microfluidic devices" Talanta 56:267-287; Becker et al., 2000, and other references cited herein and found in the scientific and patent literature.

i. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 μm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 μm, 1 μm, 2 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels may have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, and 250 μm.

Elastomeric layers may be cast thick for mechanical stability. In an exemplary embodiment, a layer is 50 microns to over a centimeter thick, and more preferably approximately 4 mm thick. A non-exclusive list of ranges of thickness of the elastomer layer in accordance with other embodiments of the present invention is between about 0.1 micron to 1 cm, 1 micron to 1 cm, 10 microns to 0.5 cm, 100 microns to 10 mm.

Membranes separating flow channels have a typical thickness of between about 0.01 and 1000 microns, more preferably 0.05 to 500 microns, more preferably 0.2 to 250, more preferably 1 to 100 microns, more preferably 2 to 50 microns, and more preferably 5 to 40 microns, and most preferably 10-25 μm. Exemplary membrane thicknesses include 0.01 μm, 0.02 μm, 0.03 μm, 0.05 μm, 0.1 μm, 0.2 μm, 0.3 μm, 0.5 μm, 1 μm, 2 μm, 3 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, 250 μm, 300 μm, 400 μm, 500 μm, 750 μm, and 1000 μm.

ii. Mixing/Reaction Chambers

As noted above, the mixing/reaction chambers may be formed in either a rigid plastic top layer or an underlying elastomeric layer. The top and sidewall surfaces of the chamber may be defined in the rigid plastic layer by forming a recess in the surface of that layer that contacts the elastomeric layer. The bottom surface of the mixing/reaction chamber is then formed by the surface of the elastomeric layer in contact with the rigid plastic layer.

In additional embodiments, the mixing/reaction chamber may be completely or primarily formed in the underlying elastomeric layer. For example, all of the top, bottom, and sidewall surfaces of the chamber may be defined by the elastomeric layer. Alternatively, the bottom and sidewall surfaces may be formed in the elastomeric layer while the inside top surface of the chamber is defined by the rigid plastic top layer of the device.

Reaction chamber dimensions in a microfluidic device can vary over a broad range. In embodiments of the present invention, reaction volumes ranging from 10 picoliters to 100 nanoliters are utilized. In some embodiments, reaction volumes greater than 100 nanoliters are utilized. Reaction chambers may also be in the microliter, nanoliter, picoliter, femtoliter or lower range of volume. In one embodiment, the reaction chamber volume is between 1-1000 femtoliters. Merely by way of example, in an embodiment, the methods and systems of the present invention are utilized with reaction volumes of 10 picoliters, 50 picoliters, 100 picoliters, 250 picoliters, 500 picoliters, and 1 nanoliter. In alternative embodiments, reaction volumes of 2 nanoliters, 5 nanoliters, 10 nanoliters, 20 nanoliters, 30 nanoliters, 40 nanoliters, 50 nanoliters, 75 nanoliters, and 100 nanoliters are utilized. In another embodiment, the reaction chamber volume is between 1-1000 picoliters. In another embodiment, the reaction chamber volume is between 0.01-100 nanoliters, preferably between 1-75 nanoliters. In one embodiment the reaction chamber volume is about 50 nanoliters. In one embodiment the reaction chamber volume is about 7.6 nanoliters. In another embodiment, the reaction chamber volume is 6 nL. The volume defined for the first solution in the flow channel (the slug volume or carry-on volume) is a fraction of the reaction chamber volume. In various embodiments, the fraction may be ⅞, ¾, ⅝, ½, ⅜, ¼, ⅕, ⅛, 1/10, 1/12, 1/20, 1/25, 1/50, 1/100, or less of the total reaction chamber volume. Preferably the fraction is less than ½, more preferably less than ¼, more preferably less than ⅛. In some embodiments the volume of reagent solution is about 1/10th the volume of the reaction chamber and the volume of the sample solution is about 9/10th of the volume of the reaction chamber.

Reaction chambers are often cuboid due in part to relative ease of manufacture, however other shapes can be used. In preferred embodiments the chamber comprises internal edges (i.e., is not spherical). These edges enhance mixing of reagent and sample. A cuboid chamber has 12 internal edges. In one embodiment the reagent chamber has at least 2 internal edges (e.g., a cylinder). More often the chamber has at least 10, at least 12, at least 14, at least 16, or at least 20 internal edges.

iii. Elastomeric Valves

As discussed above, in preferred embodiments the microfluidic device comprises elastomeric materials and monolithic valves, such as a pressure-actuated "elastomeric valve." A pressure-actuated elastomeric valve consists of a configuration in which two microchannels are separated by an elastomeric segment that can be deflected into or retracted from one of the channels (e.g., a flow channel) in response to an actuation force applied to the other channel (e.g., a control channel). Examples of elastomeric valves include upwardly-deflecting valves (see, e.g., US 20050072946), downwardly deflecting valves (see, e.g., U.S. Pat. No. 6,408,878), side actuated valves (see, e.g., US 20020127736, e.g., paragraphs 0215-0219), normally-closed valves (see, e.g., U.S. Pat. No. 6,408,878 B2 and U.S. Pat. No. 6,899,137) and others. In some embodiments a device can have a combination of valves (e.g., upwardly deflecting valves and downwardly deflecting valves). Valves can be actuated by injecting gases (e.g., air, nitrogen, and argon), liquids (e.g., water, silicon oils, perfluoropolyalkylether, and other oils), solutions containing salts and/or polymers (including but not limited to polyethylene glycol, glycerol and carbohydrates) and the like into the control channel. Some valves can be actuated by applying a vacuum to the control channel.

iv. Multilayer Soft Lithography Construction Techniques and Materials

The microfluidic devices disclosed herein may be constructed in part from elastomeric materials and constructed by single and multilayer soft lithography (MSL) techniques and/or sacrificial-layer encapsulation methods (see, e.g., Unger et al., 2000, *Science* 288:113-116, and PCT Publication WO 01/01025, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al., 2000, *Science* 288:113-116, PCT Publications WO/02/43615 and WO 01/01025, and other references cited herein and known in the art.

Soft Lithographic Bonding:

When elastomeric layers are bonded together chemically, the bonding may use chemistry that is intrinsic to the polymers comprising the patterned elastomer layers. For example, the bonding comprises two component "addition cure" bonding.

In one aspect, the various layers of elastomer are bound together in a heterogenous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly(dimethylsiloxane)", *Analytical Chemistry* (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Elastomeric layers may be created by spin-coating an RTV mixture on microfabricated mold at 2000 rpm for 30 seconds yielding a thickness of approximately 40 microns. Additional elastomeric layers may be created by spin-coating an RTV mixture on microfabricated mold. Both layers may be separately baked or cured at about 80° C. for 1.5 hours. The additional elastomeric layer may be bonded onto first elastomeric layer at about 80° C. for about 1.5 hours.

Suitable Elastomeric Materials:

Allcock et al, Contemporary Polymer Chemistry, 2nd Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus.

The elastomeric layers found in embodiments of the present invention may be fabricated from a wide variety of elastomers. In an exemplary aspect, elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones. A non-exclusive list of elastomeric materials which may be utilized in connection with the present invention includes polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), perfluoropolyalkylether siloxane block copolymer, poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene)copolymer (Viton), elastomeric compositions of polyvinylchloride (PVC), polysulfone, polycarbonate, polymethylmethacrylate (PMMA), and polytertrafluoro-ethylene (Teflon).

a. Polyisoprene, Polybutadiene, Polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

b. Polyisobutylene:

Pure polyisobutylene has no double bonds, but is crosslinked to use as an elastomer by including a small amount (≈1%) of isoprene in the polymerization. The isoprene monomers give pendant double bonds on the polyisobutylene backbone, which may then be vulcanized as above.

c. Poly(Styrene-Butadiene-Styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

d. Polyurethanes:

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

e. Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

Cross Linking Agents:

In addition to the use of the simple "pure" polymers discussed above, crosslinking agents may be added. Some agents (like the monomers bearing pendant double bonds for vulcanization) are suitable for allowing homogeneous (A to A) multilayer soft lithography or photoresist encapsulation; in such an approach the same agent is incorporated into both elastomer layers. Complementary agents (i.e. one monomer bearing a pendant double bond, and another bearing a pendant Si—H group) are suitable for heterogeneous (A to B) multilayer soft lithography. In this approach complementary agents are added to adjacent layers.

Other Materials:

In addition, polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical may also be used.

Doping and Dilution:

Elastomers may also be "doped" with uncrosslinkable polymer chains of the same class. For instance RTV 615 may be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "inert" polymer chains, so this is called "dilution". RTV 615 cures at up to 90% dilution, with a dramatic reduction in Young's modulus.

Other examples of doping of elastomer material may include the introduction of electrically conducting or magnetic species, as described in detail below in conjunction with alternative methods of actuating the membrane of the device. Should it be desired, doping with fine particles of material having an index of refraction different than the elastomeric material (i.e. silica, diamond, sapphire) is also contemplated as a system for altering the refractive index of the material. Strongly absorbing or opaque particles may be added to render the elastomer colored or opaque to incident radiation, which may be of benefit in an optically addressable system.

Finally, by doping the elastomer with specific chemical species, these doped chemical species may be presented at the elastomer surface, thus serving as anchors or starting points for further chemical derivitization.

v. Vent Channels

The microfluidic devices may have "vent channels" positioned to accelerate or facilitate withdrawal of gas from the reaction chamber or channels to facilitate filling (e.g., dead-end or blind filling). See PCT Publication WO 2006/071470, incorporated herein by reference. A vent channel system comprises channels separated from, e.g., a sample (or reagent) bus line by a thin gas permeable (e.g., elastomeric) membrane. The vent channels typically lie over or under a bus line (e.g., in a vent layer or control layer). Vapor and gasses are expelled out of the bus line by passing through an intervening gas permeable material (such as an elastomer), and enters the vent channels(s). Vapor and gasses can diffuse into the vent channel or removal can be accelerated by reducing the pressure in the vent channel relative to the bus line. This reduction can be achieved, for example, by flowing dry gas (e.g., air or $N_2$) through the vent channel(s) or drawing a vacuum through the channel(s), or by any other method that reduces vent channel pressure (including reduction caused by Bernoulli's principle).

The dimensions of vent channels can vary widely. In an exemplary aspect, vent channels have at least one cross-sectional dimension in the range of 0.05 to 1000 microns, often 10 to 500 microns, and most often 50 to 200 microns. In some embodiments, the channel height is not more than about 500 microns or less than about 20 microns (in some embodiments, not more than about 250 microns or less than about 50 microns) and the channel width is not more than 5000 microns or less than 20 microns). In one embodiment, vent channels have rectangular cross-sectional dimensions of about 15 microns×50 microns. In some embodiments, vent channels preferably have width-to-depth ratios of about 1:10 to 100:1, such as between about 2:1 and 1:2, and sometimes about 1:1. In embodiments in which a vacuum is applied to a vent channel dimensions may be selected to avoid collapse of the channel under vacuum (e.g., higher height:width ratios). However, the vent channels are not limited to these particular dimensions or proportions.

As noted above, in some embodiments, the lumen of the vent channel(s) is separated from the interior of the bus line by less than 1000 microns, such as from 0.05 to 1000 microns, often from 1 to 500 microns, often from 1 to 200 microns, and most often from 5 to 50 microns. In one embodiment, a vent is placed below the sample bus line consisting of a group of six 15×50 micron channels separated from the bus line by a 15 micron membrane (gas-permeable). In another embodiment the bus line hexfurcates into six parallel lines (each 50 microns wide) that cross over the six vent lines, thus increasing the amount of membrane area to facilitate vapor and/or gas expulsion.

With reference to an elastomeric or partially elastomeric device, a system of vent channel can lie in an elastomer layer one side of which constitutes a portion of the interior surface of the bus line. For example, in a "wholly" elastomeric device the vent channels may lie in the elastomer layer above or below the flow channel layer (and, for devices with control channels, on the side of the flow layer opposite the control channel layer or in the control channel layer). Vent channels may also be incorporated into the flow channel layer. In some embodiments, providing vent channels above the bus line is the optimal arrangement. However, it is generally easier to fabricate an MSL chip with the vent below the bus line (e.g., as part of the control layer).

vi. Characteristics and Fabrication of Hybrid and Non-Elastomeric Devices

As noted, a variety of materials can be used in fabrication of microfluidic devices. Devices can be fabricated from combinations of materials. In a hybrid device channels and/or the reaction chamber may be formed from a non-elastomeric substrate, but the channels and/or the reaction chamber have an elastomeric component sufficient that allows the chambers or reaction channels to be blind filled. For example, in some embodiments the walls and ceiling of a reaction chamber and/or flow channels are elastomeric and the floor of the reactor is formed from an underlying nonelastomeric substrate (e.g., glass), while in other embodiments, both the walls and floors of the reaction chamber and/or flow channels are constructed from a nonelastomeric material, and only the ceiling of the reaction chamber and/or flow channels is constructed from elastomer. These channels and chambers are sometimes referred to as "composite structures." See, e.g., US 20020127736. A variety of approaches can be employed to seal the elastomeric and nonelastomeric components of a device, some of which are described in U.S. Pat. No. 6,719,868 and US 20020127736, paragraph [0227] et seq.

Valves of various types are known in the art, including micromechanical valves, elastomeric valves, solid-state microvalves, and others. See, e.g., Felton, 2003, The New Generation of Microvalves" *Analytical Chemistry* 429-432. Two common approaches to fabrication of microelectromechanical (MEMS) structures such as pumps and valves are silicon-based bulk micro-machining (which is a subtractive fabrication method whereby single crystal silicon is lithographically patterned and then etched to form three-dimensional structures), and surface micro-machining (which is an additive method where layers of semiconductor-type materials such as polysilicon, silicon nitride, silicon dioxide, and various metals are sequentially added and patterned to make three-dimensional structures).

In addition to elastomeric valves actuated by pressure-based actuation systems, monolithic valves with an elastomeric component and electrostatic, magnetic, electrolytic and electrokinetic actuation systems may be used. See, e.g., US 20020109114; US 20020127736, e.g., at ¶¶ 0168-0176; and U.S. Pat. No. 6,767,706 B2 e.g., at §6.3. Likewise other types of valves are known in the art and may be used. See, e.g. Jeon et al. U.S. Pat. No. 6,767,194, incorporated herein by reference, and Luo et al. 2003, "Monolithic valves for microfluidic chips based on thermoresponsive polymer gels" *Electrophoresis* 24:3694-3702.

VII. Exemplary Reactions

Embodiments of the devices, systems and methods described are useful for any microfluidic process that involves combining mixing two or more solutions. A number of reactions useful for detection, quantitation and analysis of nucleic acids are described below in this section. However, the uses of a microfluidic device are not limited to "reactions" of this type. Other "reactions" include, but are not limited to, binding interactions (e.g., ligand-antiligand interactions, including antibody-antigen interactions, avidin-biotin interactions), protein-ligand interactions and interactions between cells and various compounds, trapping, chemical or biochemical synthesis, analysis of cells or viruses, and others.

Nucleic acid amplification reactions can be carried out using the microfluidic devices and methods described. For example, devices of the invention may be designed to conduct thermal cycling reactions. PCR is perhaps the best known amplification technique. The devices utilized in embodiments of the present invention are not limited to conducting PCR amplifications. Other types of amplification reactions that can be conducted include, but are not limited to, (i) ligase chain reaction (LCR) (see Wu and Wallace, *Genomics* 4:560 (1989) and Landegren et al., *Science* 241:1077 (1988)); (ii) transcription amplification (see Kwoh et al., *Proc. Natl. Acad. Sci. USA* 86:1173 (1989)); (iii) self-sustained sequence replication (see Guatelli et al., *Proc. Nat. Acad. Sci. USA*, 87:1874 (1990)); and (iv) nucleic acid based sequence amplification (NASBA) (see, Sooknanan, R. and Malek, L., *BioTechnology* 13: 563-65 (1995)).

Amplification products (amplicons) can be detected and distinguished (whether isolated in a reaction chamber or at any subsequent time) using routine methods for detecting nucleic acids. Many different signal moieties may be used in various embodiments of the present invention. For example, signal moieties include, but are not limited to, fluorophores, radioisotopes, chromogens, enzymes, antigens, heavy metals, dyes, phosphorescence groups, chemiluminescent groups, minor grove binding probes, and electrochemical detection moieties. Exemplary fluorophores that may be used as signal moieties include, but are not limited to, rhodamine, cyanine 3 (Cy 3), cyanine 5 (Cy 5), fluorescein, VIC™, LIZ™, Tamra™, 5-FAM™, 6-FAM™, and Texas Red (Molecular Probes). (VIC™, LIZ™, Tamra™, 5-FAM™, and 6-FAM™ (all available from Applied Biosystems, Foster City, Calif.). Exemplary radioisotopes include, but are not limited to, $^{32}P$, $^{33}P$, and $^{35}S$. Signal moieties also include elements of multi-element indirect reporter systems, e.g., biotin/avidin, antibody/antigen, ligand/receptor, enzyme/substrate, and the like, in which the element interacts with other elements of the system in order to effect a detectable signal. Certain exemplary multi-element systems include a biotin reporter group attached to a probe and an avidin conjugated with a fluorescent label. Detailed protocols for methods of attaching signal moieties to oligonucleotides can be found in, among other places, G. T. Hermanson, Bioconjugate Techniques, Academic Press, San Diego, Calif. (1996) and S. L. Beaucage et al., Current Protocols in Nucleic Acid Chemistry, John Wiley & Sons, New York, N.Y. (2000).

Amplicons comprising double-stranded DNA can be detected using intercalation dyes such as SYBR™, Pico Green (Molecular Probes, Inc., Eugene, Oreg.), ethidium bromide and the like (see Zhu et al., 1994, *Anal. Chem.* 66:1941-48) and/or gel electrophoresis. More often, sequence-specific detection methods are used (i.e., amplicons are detected based on their nucleotide sequence). Examples of detection methods include hybridization to arrays of immobilized oligo or polynucleotides, and use of differentially labeled molecular beacons or other "fluorescence resonance energy transfer" (FRET)-based detection systems. FRET-based detection is a preferred method for detection according to some embodiments of the present invention. In FRET-based assays a change in fluorescence from a donor (reporter) and/or acceptor (quencher) fluorophore in a donor/acceptor fluorophore pair is detected. The donor and acceptor fluorophore pair are selected such that the emission spectrum of the donor overlaps the excitation spectrum of the acceptor. Thus, when the pair of fluorophores are brought within sufficiently close proximity to one another, energy transfer from the donor to the acceptor can occur and can be detected. A variety of assays are known including, for example and not limitation, template extension reactions, quantitative RT-PCR, Molecular Beacons, and Invader assays, these are described briefly below.

FRET and template extension reactions utilize a primer labeled with one member of a donor/acceptor pair and a nucleotide labeled with the other member of the donor/acceptor pair. Prior to incorporation of the labeled nucleotide into the primer during an template-dependent extension reaction, the donor and acceptor are spaced far enough apart that energy transfer cannot occur. However, if the labeled nucleotide is incorporated into the primer and the spacing is sufficiently close, then energy transfer occurs and can be detected. These methods are particularly useful in conducting single base pair extension reactions in the detection of single nucleotide polymorphisms and are described in U.S. Pat. No. 5,945,283 and PCT Publication WO 97/22719. The reactions can optionally be thermocycled to increase signal using the temperature control methods and apparatus described throughout the present specification.

A variety of so-called "real time amplification" methods or "real time quantitative PCR" methods can also be used to determine the quantity of a target nucleic acid present in a sample by measuring the amount of amplification product formed during or after the amplification process itself. Fluorogenic nuclease assays are one specific example of a real time quantitation method which can be used successfully with the devices described herein. This method of monitoring the formation of amplification product involves the continuous measurement of PCR product accumulation using a dual-labeled fluorogenic oligonucleotide probe—an approach frequently referred to in the literature as the "TaqMan" method. See, for example, U.S. Pat. No. 5,723,591.

With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye. In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use are described further, for example, by Piatek et al., 1998, *Nat. Biotechnol.* 16:359-63; Tyagi, and Kramer, 1996, *Nat. Biotechnology* 14:303-308; and Tyagi, et al., 1998, *Nat. Biotechnol.* 16:49-53 (1998).

The Scorpion detection method is described, for example, by Thelwell et al. 2000, Nucleic Acids Research, 28:3752-3761 and Solinas et al., 2001, "Duplex Scorpion primers in SNP analysis and FRET applications" *Nucleic Acids Research* 29:20. Scorpion primers are fluorogenic PCR primers with a probe element attached at the 5'-end via a PCR stopper. They are used in real-time amplicon-specific detection of PCR products in homogeneous solution. Two different formats are possible, the 'stem-loop' format and the 'duplex' format. In both cases the probing mechanism is intramolecular. The basic elements of Scorpions in all formats are: (i) a PCR primer; (ii) a PCR stopper to prevent PCR read-through of the probe element; (iii) a specific probe sequence; and (iv) a fluorescence detection system containing at least one fluorophore and quencher. After PCR extension of the Scorpion primer, the resultant amplicon contains a sequence that is complementary to the probe, which is rendered single-stranded during the denaturation stage of each PCR cycle. On cooling, the probe is free to bind to this complementary sequence, producing an increase in fluorescence, as the quencher is no longer in the vicinity of the fluorophore. The PCR stopper prevents undesirable read-through of the probe by Taq DNA polymerase.

Invader assays (Third Wave Technologies, Madison, Wis.) are used particularly for SNP genotyping and utilize an oligonucleotide, designated the signal probe that is complementary to the target nucleic acid (DNA or RNA) or polymorphism site. A second oligonucleotide, designated the Invader Oligo, contains the same 5' nucleotide sequence, but the 3' nucleotide sequence contains a nucleotide polymorphism. The Invader Oligo interferes with the binding of the signal probe to the target nucleic acid such that the 5' end of the signal probe forms a "flap" at the nucleotide containing the polymorphism. This complex is recognized by a structure specific endonuclease, called the Cleavase enzyme. Cleavase cleaves the 5' flap of the nucleotides. The released flap binds with a third probe bearing FRET labels, thereby forming another duplex structure recognized by the Cleavase enzyme. This time the Cleavase enzyme cleaves a fluorophore away from a quencher and produces a fluorescent signal. For SNP genotyping, the signal probe will be designed to hybridize with either the reference (wild type) allele or the variant (mutant) allele. Unlike PCR, there is a linear amplification of signal with no amplification of the nucleic acid. Further details sufficient to guide one of ordinary skill in the art are provided by, for example, Neri, B. P., et al., Advances in Nucleic Acid and Protein Analysis 3826:117-125, 2000) and U.S. Pat. No. 6,706,471.

A variety of multiplex amplification systems can be used in conjunction with the present invention. In one type, several different targets can be detected simultaneously by using multiple differently labeled probes each of which is designed to hybridize only to a particular target. Since each probe has a different label, binding to each target to be detected based on the fluorescence signals. By judicious choice of the different labels that are utilized, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Gene Expression

Gene expression analysis involves determining the level at which one or more genes is expressed in a particular cell. The determination can be qualitative, but generally is quantitative. In a differential gene expression analysis, the levels of the gene(s) in one cell (e.g., a test cell) are compared to the expression levels of the same genes in another cell (control cell). A wide variety of such comparisons can be made. Examples include, but are not limited to, a comparison between healthy and diseased cells, between cells from an individual treated with one drug and cells from another untreated individual, between cells exposed to a particular toxicant and cells not exposed, and so on. Genes whose expression levels vary between the test and control cells can serve as markers and/or targets for therapy. For example, if a certain group of genes is found to be up-regulated in diseased cells rather than healthy cells, such genes can serve as markers of the disease and can potentially be utilized as the basis for diagnostic tests. These genes could also be targets. A strategy for treating the disease might include procedures that result in a reduction of expression of the up-regulated genes.

The design of the devices enables them to be utilized in combination with a number of different heating systems. Thus, the devices are useful in conducting diverse analyses that require temperature control. Additionally, those microfluidic devices adapted for use in heating applications can incorporate a further design feature to minimize evaporation of sample from the reaction sites. Devices of this type in general include a number of guard channels and/or reservoirs or chambers formed within the elastomeric device through which water can be flowed to increase the water vapor pressure within the elastomeric material from which the device is formed, thereby reducing evaporation of sample material from the reaction sites.

In another embodiment, a temperature cycling device may be used to control the temperature of the microfluidic devices. Preferably, the microfluidic device would be adapted to make thermal contact with the microfluidic device. Where the microfluidic device is supported by a substrate material, such as a glass slide or the bottom of a carrier plate, such as a plastic carrier, a window may be formed in a region of the carrier or slide such that the microfluidic device, preferably a device having an elastomeric block, may directly contact the heating/cooling block of the temperature cycling device. In a preferred embodiment, the heating/cooling block has grooves therein in communication with a vacuum source for applying a suction force to the microfluidic device, preferably a portion adjacent to where the reactions are taking place. Alternatively, a rigid thermally conductive plate may be bonded to the microfluidic device that then mates with the heating and cooling block for efficient thermal conduction resulting.

The array format of certain of the devices means the devices can achieve high throughput. Collectively, the high throughput and temperature control capabilities make the devices useful for performing large numbers of nucleic acid amplifications (e.g., polymerase chain reaction (PCR)). Such reactions will be discussed at length herein as illustrative of the utility of the devices, especially of their use in any reaction requiring temperature control. However, it should be understood that the devices are not limited to these particular applications. The devices can be utilized in a wide variety of other types of analyses or reactions.

If the device is to be utilized in temperature control reactions (e.g., thermocycling reactions), then, as described in greater detail infra, the elastomeric device is typically fixed to a support (e.g., a glass slide). The resulting structure can then be placed on a temperature control plate, for example, to control the temperature at the various reaction sites. In the case of thermocycling reactions, the device can be placed on any of a number of thermocycling plates.

Because the devices are made of elastomeric materials that are relatively optically transparent, reactions can be readily monitored using a variety of different detection systems at essentially any location on the microfluidic device. Most typically, however, detection occurs at the reaction site itself (e.g., within a region that includes an intersection of flow channels or at the blind end of a flow channel). The fact that the device is manufactured from substantially transparent materials also means that certain detection systems can be utilized with the current devices that are not usable with traditional silicon-based microfluidic devices. Detection can be achieved using detectors that are incorporated into the device or that are separate from the device but aligned with the region of the device to be detected.

Operating microfluidic devices with such small reaction volumes reduces reagent usage as well as sample usage. Moreover, some embodiments of the present invention provide methods and systems adapted to perform real-time detection, when used in combination with real-time quantitative PCR. Utilizing these systems and methods, six orders of linear dynamic range are provided for some applications as well as quantitative resolution high enough to allow for the detection of sub-nanoMolar fluorophore concentrations in 10 nanoliter volumes. One of ordinary skill in the art would recognize many variations, modifications, and alternatives.

Reactions may be designed to produce a detectable signal (indication) including fluorescent indications, but luminescent indications, including chemiluminescent, electroluminescent, electrochemiluminescent, and phospholumi-nescent, bioluminescent, and other luminescent processes, or any other processing involving any other type of indications that may be detected using a detection device. As will be evident to one of skill in the art, methods and systems operable in the detection and analysis of these fluorescent and luminescent indications are transferable from one indication to another. Additionally, although some embodiments of the present invention utilize spectral filters as optical elements, this is not required by the present invention. Some fluorescent and luminescent applications do not utilize spectral filters in the optical excitation path, the optical emission path, or both. As described herein, other embodiments utilize spectral filters. One of skill in the art will appreciate the differences associated with particular applications.

In some embodiments, a variety of devices and methods for conducting microfluidic analyses are utilized herein, including devices that can be utilized to conduct thermal cycling reactions such as nucleic acid amplification reactions. The devices differ from conventional microfluidic devices in that they include elastomeric components; in some instances, much or all of the device is composed of elastomeric material. For example, amplification reactions can be linear amplifications, (amplifications with a single primer), as well as exponential amplifications (i.e., amplifications conducted with a forward and reverse primer set).

VIII. Examples

A microfluidic device having multiple vent channel designs was tested for the effectiveness of the vent channels during blind fill loading of the mixing/reacting chambers, as well as checking for significant dehydration during thermal cycling, such as the device would experience during a PCR application. The vent channel designs being tested included (1) a single vent under the chamber, (2) Multiple vents under the chamber, (3) a radial vent under the chamber, and (4) a radial vent with expansion volume (see FIG. 13). The microfluidic device had one elastomeric PDMS layer for fluid channels (red) and another PDMS layer for vent channels (blue).

The initial tests with the microfluidic device showed that blind filling of the mixing/reacting chambers worked, but that significant dehydration occurred during thermal cycling. The addition of aluminum foil tape to the bottom of the device was used to prevent the dehydration.

The microfluidic device was made with chambers machined into a Zeonor® plate. A three-layer DC Topaz MSL was bonded to the Zeonor® plate that enables blind filling and venting at normal process fill times and pressures. An IHS made of aluminum foil tape was used that prevents dehydration. The device was filled with standard 1×PCR (premixed) and run on a BioMark 1 instrument with standard protocol. Thermal contact was made to the instrument using an additional layer of aluminum foil and silicone heat grease. Images were ripped and data processed using a custom MatLab algorithm.

The test results demonstrated that the single vent scheme (vent channel design #1) consistently failed to blind load. There was a large bubble in the center of twelve out of twelve chambers. During thermal cycling, this bubble did not move nor grow significantly, indicating that dehydration does not occur on this design. All 24 remaining chambers filled properly and did not develop bubbles. This indicates that the three other vent channel designs tested (vent channel designs #2-4) are acceptable candidates for blind loading.

Figure 13:
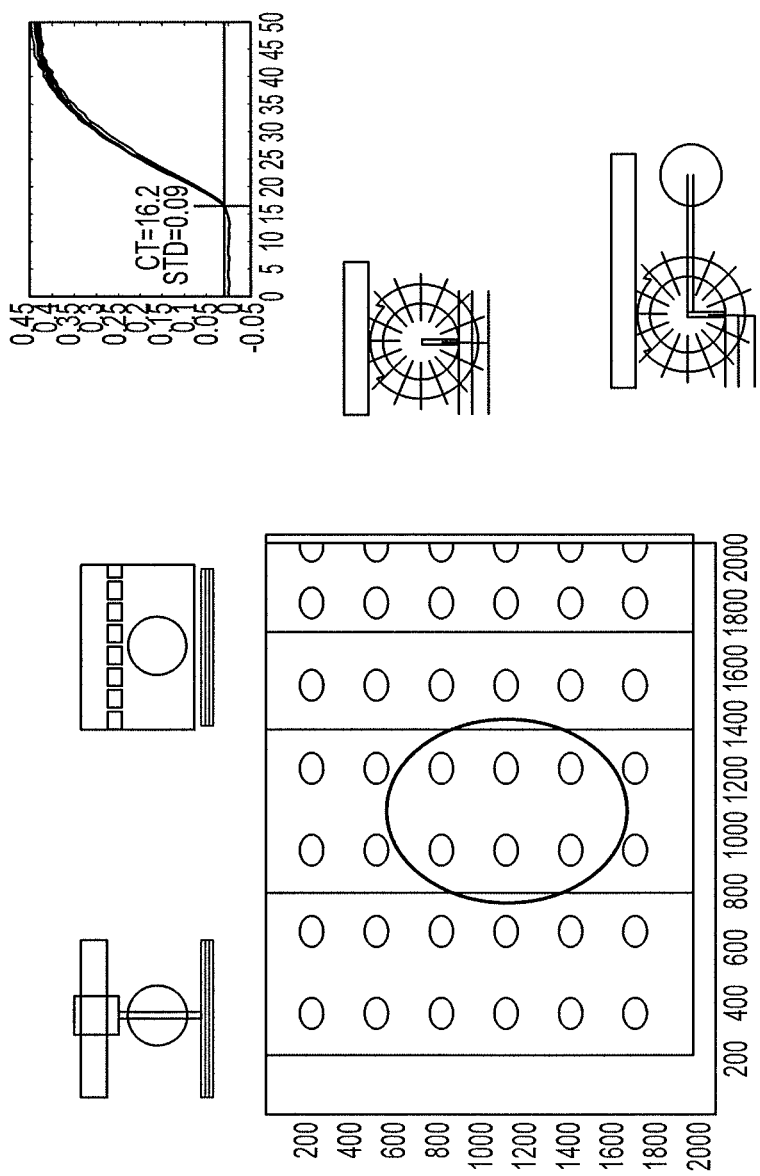
FIG. 13 shows test results for various configurations of vent channels in a microfluidic device used to perform PCR experiments.
Figure 14:
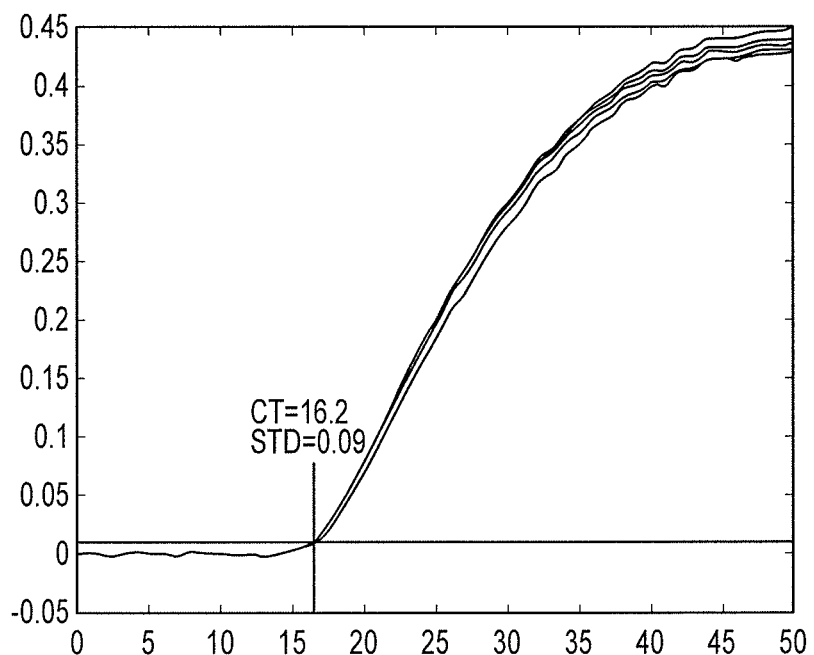
FIG. 14 shows a graph of PCR curves from the PCR experiments.

The fluorescent image in FIG. 13 shows a substantial and non-uniform background due to the acrylic adhesive of the aluminum foil tape IHS. Because of this, no effort to subtract the background was made. The FAM over ROX value, baseline subtracted, is plotted in FIG. 14. Here six of the chambers are shown to have classic PCR growth curves with a mean count of 16.2, and a standard deviation of 0.09.

The results here show that a using a microfluidic device with a hard plastic Zeonor plate top layer enables high volume production at the lowest cost without the need to punch the pour layer.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the chamber" includes reference to one or more chambers and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

The invention having now been described by way of written description and example, those of skill in the art will recognize that the invention can be practiced in a variety of embodiments and that the foregoing description and examples are for purposes of illustration and not limitation of the following claims.

What is claimed is:

1. A method of filling a reaction chamber comprising
   a) providing a microfluidic device comprising:
      a rigid base layer;
      an elastomeric layer on the base layer, wherein the elastomeric layer comprises at least part of: (i) a fluid channel for transporting a liquid reagent, wherein the fluid channel is at least partly in the elastomeric layer (ii) a gas containing chamber fluidically connected to the fluid channel, wherein the chamber channel is at least partly in the elastomeric layer and (iii) a vent channel separated from the fluid channel or chamber by an elastomeric membrane, wherein the fluid channel is at least partly in the elastomeric layer;
      a rigid plastic layer on the elastomeric layer;
   b) filling the chamber with fluid, wherein as a result of said filling at least a portion of the gas in the chamber is displaced from the chamber and diffuses through the elastomeric membrane from the chamber to the vent channel; thereby transporting in the vent channel at least a portion of the displaced gas that has diffused through the elastomeric layer from the chamber.

2. The method of claim 1 wherein the microfluidic device comprises:
   the rigid base layer;
   the elastomeric layer on the base layer, wherein the elastomeric layer comprises at least part of a fluid channel for transporting a liquid reagent, and the vent channel that accepts gas diffusing through the elastomeric layer from the fluid channel and vents it out of the elastomeric layer;
   the mixing chamber fluidly connected to the fluid channel;
   a control channel in the elastomeric layer overlapping with a deflectable elastomeric membrane that defines a portion of the fluid channel, wherein the control channel is operable to change a rate at which the liquid reagent flows through the fluid channel, and wherein the fluid channel and control channel are in different levels of the elastomeric layer; and
   the rigid plastic layer on the elastomeric layer.

3. The method of claim 1 comprising:
   providing a microfluidic device comprising an elastomeric layer positioned between two gas impermeable layers, wherein the device comprises a slug channel formed in the elastomeric layer and fluidly coupled to the reaction chamber, and a vent channel;
   isolating a first portion of the slug channel from the second portion of the slug channel by closing a first valve partitioning the first and second portions of the slug channel;
   filling the first portion of the slug chamber with a first fluid, and the second portion of the slug chamber with a second fluid;
   opening a second valve between the slug channel and the reaction chamber to inject at least a portion of the first and second fluids into the reaction chamber, wherein the injection of the first and second fluids displaces at least a portion of gases in the reaction chamber; and
   transporting in the vent channel at least a portion of the displaced gases that have diffused through the elastomeric layer from the reaction chamber.

4. The method of claim 1, wherein the displaced gases are transported out of the elastomeric layer by the vent channel.

* * * * *